(12) United States Patent
Dahl et al.

(10) Patent No.: US 11,543,417 B2
(45) Date of Patent: Jan. 3, 2023

(54) CHIP-SEQ ASSAYS

(71) Applicant: Oslo universitetssykehus HF, Oslo (NO)

(72) Inventors: John Arne Dahl, Oslo (NO); Arne Klungland, Oslo (NO)

(73) Assignee: OSLO UNIVERSITETSSYKEHUS HF, Oslo (NO)

( * ) Notice: Subject to any disclaimer, the term of this patent is extended or adjusted under 35 U.S.C. 154(b) by 565 days.

(21) Appl. No.: 16/328,909

(22) PCT Filed: Aug. 29, 2017

(86) PCT No.: PCT/IB2017/001198
§ 371 (c)(1),
(2) Date: Feb. 27, 2019

(87) PCT Pub. No.: WO2018/042251
PCT Pub. Date: Mar. 8, 2018

(65) Prior Publication Data
US 2021/0285961 A1    Sep. 16, 2021

Related U.S. Application Data

(60) Provisional application No. 62/380,812, filed on Aug. 29, 2016.

(51) Int. Cl.
*C12N 15/10* (2006.01)
*C12Q 1/6804* (2018.01)
*G01N 33/68* (2006.01)

(52) U.S. Cl.
CPC ..... *G01N 33/6875* (2013.01); *C12N 15/1093* (2013.01); *C12Q 1/6804* (2013.01)

(58) Field of Classification Search
CPC ........... G01N 33/6875; G01N 33/5306; C12N 15/1093; C12Q 1/6804
See application file for complete search history.

(56) References Cited

U.S. PATENT DOCUMENTS

| | | | |
|---|---|---|---|
| 5,912,148 A | 6/1999 | Eggerding |
| 6,130,073 A | 10/2000 | Eggerding |
| 6,210,891 B1 | 4/2001 | Nyren et al. |
| 6,258,568 B1 | 7/2001 | Nyren et al. |
| 6,818,395 B1 | 11/2004 | Quake et al. |
| 6,833,246 B2 | 12/2004 | Balasubramanian |
| 6,911,345 B2 | 6/2005 | Quake et al. |
| 6,969,488 B2 | 11/2005 | Bridgham et al. |
| 7,115,400 B1 | 10/2006 | Adessi et al. |

(Continued)

FOREIGN PATENT DOCUMENTS

WO    WO1999/9906592    2/1999

OTHER PUBLICATIONS

Rotem et al. (Nature Biotechnology, 2015, 33(11):1165-1175) (Year: 2015).*

(Continued)

*Primary Examiner* — Jeremy C Flinders
(74) *Attorney, Agent, or Firm* — Casimir Jones S.C.; J. Mitchell Jones

(57) ABSTRACT

In some embodiments, the present invention provides chromatin immunoprecipitation (ChIP) methods. In particular, the present invention provides methods and compositions for performing ChIP (e.g., ChIP-seq) assays on small numbers or cells.

18 Claims, 9 Drawing Sheets

(56) References Cited

U.S. PATENT DOCUMENTS

| | | |
|---|---|---|
| 7,169,560 B2 | 1/2007 | Lapidus et al. |
| 7,170,050 B2 | 1/2007 | Turner et al. |
| 7,282,337 B1 | 10/2007 | Harris |
| 7,302,146 B2 | 11/2007 | Turner et al. |
| 7,313,308 B2 | 12/2007 | Turner et al. |
| 7,315,019 B2 | 1/2008 | Turner et al. |
| 7,329,492 B2 | 2/2008 | Hardin et al. |
| 7,405,281 B2 | 7/2008 | Xu et al. |
| 7,476,503 B2 | 1/2009 | Turner et al. |
| 7,482,120 B2 | 1/2009 | Buzby |
| 7,501,245 B2 | 3/2009 | Quake et al. |
| 7,668,697 B2 | 2/2010 | Volkov et al. |
| 8,715,951 B2 | 5/2014 | Parhami-Seren |
| 2007/0036511 A1 | 2/2007 | Lundquist et al. |
| 2007/0072196 A1 | 3/2007 | Xu et al. |
| 2007/0077564 A1 | 4/2007 | Roitman et al. |
| 2007/0128133 A1 | 6/2007 | Eid et al. |
| 2007/0134128 A1 | 6/2007 | Korlach |
| 2007/0141598 A1 | 6/2007 | Turner et al. |
| 2007/0161017 A1 | 7/2007 | Eid et al. |
| 2007/0188750 A1 | 8/2007 | Lundquist et al. |
| 2007/0196846 A1 | 8/2007 | Hanzel et al. |
| 2007/0206187 A1 | 9/2007 | Lundquist et al. |
| 2007/0231804 A1 | 10/2007 | Korlach et al. |
| 2007/0238679 A1 | 10/2007 | Rank et al. |
| 2008/0009007 A1 | 1/2008 | Lyle et al. |
| 2008/0030628 A1 | 2/2008 | Lundquist et al. |
| 2008/0032301 A1 | 2/2008 | Rank et al. |
| 2008/0050747 A1 | 2/2008 | Korlach et al. |
| 2008/0080059 A1 | 4/2008 | Dixon et al. |
| 2008/0095488 A1 | 4/2008 | Foquet et al. |
| 2008/0108082 A1 | 5/2008 | Rank et al. |
| 2008/0128627 A1 | 6/2008 | Lundquist et al. |
| 2008/0145278 A1 | 6/2008 | Korlach |
| 2008/0152280 A1 | 6/2008 | Lundquist et al. |
| 2008/0152281 A1 | 6/2008 | Lundquist et al. |
| 2008/0153095 A1 | 6/2008 | Williams et al. |
| 2008/0153100 A1 | 6/2008 | Rank et al. |
| 2008/0157005 A1 | 7/2008 | Lundquist et al. |
| 2008/0160531 A1 | 7/2008 | Korlach |
| 2008/0165346 A1 | 7/2008 | Lundquist et al. |
| 2008/0176241 A1 | 7/2008 | Eid et al. |
| 2008/0176316 A1 | 7/2008 | Eid et al. |
| 2008/0176769 A1 | 7/2008 | Rank et al. |
| 2008/0199874 A1 | 8/2008 | Otto et al. |
| 2008/0199932 A1 | 8/2008 | Hanzel et al. |
| 2008/0206764 A1 | 8/2008 | Williams et al. |
| 2008/0212960 A1 | 9/2008 | Lundquist et al. |
| 2008/0241951 A1 | 10/2008 | Battulga et al. |
| 2009/0026082 A1 | 1/2009 | Rothberg |
| 2009/0035777 A1 | 2/2009 | Kokoris et al. |
| 2009/0127589 A1 | 5/2009 | Rothberg et al. |
| 2010/0035253 A1 | 2/2010 | Gordon et al. |
| 2010/0063743 A1 | 3/2010 | Gordon et al. |
| 2010/0197507 A1 | 5/2010 | Rothberg et al. |
| 2010/0152050 A1 | 6/2010 | Gordon et al. |
| 2010/0159531 A1 | 6/2010 | Gordon et al. |
| 2010/0188073 A1 | 7/2010 | Rothberg et al. |
| 2010/0301398 A1 | 12/2010 | Rothberg et al. |
| 2010/0323350 A1 | 12/2010 | Gordon et al. |

OTHER PUBLICATIONS

Sheaffer et al. (Yi Feng and Lin Zhang (eds.), Long Non-Coding RNAs: Methods and Protocols, Methods in Molecular Biology, vol. 1402, DOI 10.1007/978-1-4939-3378-5_9, available Jan. 1, 2016) (Year: 2016).*

Assaf Rotem et al, "Single-cell ChIP-seq reveals cell subpopulations defined by chromatin state", *Nature Biotechnology* (*Advance Online Publication*),vol. 33, No. 11, Oct. 12, 2015 (Oct. 12, 2015), pp. 1165-1172.

International Search Report and Written Opinion; International Application No. PCT/IB2017/001198; dated Dec. 20, 2017; 15 pages.

Lara-Astiaso, D. et al. Immunogenetics. Chromatin state dynamics during blood formation. *Science* 345, 943-949 (2014).

Shen, J. et al. H3K4me3 epigenomic landscape derived from ChIP-Seq of 1 000 mouse early embryonic cells. *Cell Res* 25, 143-147 (2014).

\* cited by examiner

Metaphase II oocyte
(H3K4me3)

Green: H3K4me3
Blue : DAPI

CHIP-SEQ ASSAYS

CROSS-REFERENCE TO RELATED APPLICATIONS

This application claims priority to U.S. Provisional Patent Application No. 62/380,812, filed Aug. 29, 2016, the contents of which are incorporated by reference in its entirety.

FIELD OF INVENTION

In some embodiments, the present invention provides chromatin immunoprecipation (ChIP) methods. In particular, the present invention provides methods and compositions for performing ChIP (e.g., ChIP-seq) assays on small numbers of cells.

BACKGROUND

State of the art Chromatin immunoprecipation coupled with high-throughput sequencing technology (ChIP-seq) can use as little as 500 cell-equivalents of chromatin per reaction but needs 10,000 cells for initial steps (Lara-Astiaso, D. et al. Immunogenetics. Chromatin state dynamics during blood formation. *Science* 345, 943-949 (2014)), or require a highly specialized microfluidics device that is not readily available (Shen, J. et al. H3K4me3 epigenomic landscape derived from ChIP-Seq of 1 000 mouse early embryonic cells. *Cell Res* 25, 143-147 (2014)).

Improved methods for ChIP are needed. In particular, methods for performing ChIP on small numbers of cells are needed.

SUMMARY

In some embodiments, the present invention provides immunoprecipation (e.g., chromatin immunoprecipation (ChIP)) methods. In particular, the present invention provides methods and compositions for performing ChIP (e.g., ChIP-seq) assays on small numbers or cells.

For example, in some embodiments, the present invention provides a method of performing immunoprecipation (e.g., ChIP) and high throughput sequencing (ChIP-seq), comprising: a) treating (e.g., sonicating, chemically treating, or enzymatically treating (e.g., with MNase or DNase) a sample comprising a plurality of cells, tissue, biopsy samples, or embryos under conditions such that chromatin in the cells is fragmented; b) contacting the sample with an epitope binding factor (e.g., antibody) that specifically binds to a target molecule (e.g., protein or nucleic acid), wherein the antibody is free or bound to a solid support; c) contacting the sample with at least one agent that blocks non-specific binding of proteins or nucleic acids from the sample to the antibody; d) washing the sample under stringent conditions; e) generating sequencing libraries; and f) pooling the sequencing libraries. In some embodiments, the at least one agent is histones (e.g., monomers, dimers, tetramers, or octameres), non-immunized IgGs, IgGs immunized to a target that is not present in the sample, e.g. Rabbit Anti-Mouse IgG H&L (ab46540) or a combination thereof. In some embodiments, the method further comprises the step of performing a sequencing assay with the pooled sequencing library. In some embodiments, the sample of cells is 1,000,000 or less (e.g., 1,000,000, 500,000, 100,000, 50,000, 25,000, 10,000, 5000, 1000, 900, 800, 700, 600, 500, 400, 300, 200, 100, 50, 25, 10, 5, or less) cells or embryos. In some embodiments, the sample is 10 (e.g., 9, 8, 7, 6, 5, 4, 3, 2, or a single) cell or embryo or the lysate or fraction of a single cell or embryo. In some embodiments, the embryo is a 2 cell embryo, a 4 cell embryo, or an 8 cell embryo. In some embodiments, the sequencing assay is a high throughput sequencing assay or amplification (e.g., qPCR) assay. In some embodiments, the histones are histone H2A, H2B, H3 and H4 proteins with or without chemical modifications, non-target chemical modifications, and/or post translations modification. In some embodiments, the non-immunized antibody or antibody immunized to a target that is not present in the sample is of the same or different isotype as the antibody. In some embodiments, the solid support is magnetic or paramagnetic beads, agarose beads, or sepharose beads. In some embodiments, the target molecule is a protein (e.g., transcription factor or histone (e.g., H3K4me3, H3, or K27ac), DNA binding protein, RNA binding protein, or chromatin binding protein), enzymatically or chemically added marker (e.g., label), or nucleic acid. In some embodiments, the histone is cross-linked (e.g., with formaldehyde, UV, etc.) or native (e.g., not cross-linked). In some embodiments, the agent is provided at a concentration of 0.01 µg to 10 µg (e.g., 1 µg).

Further embodiments provide a kit or system, comprising: a solid support configured for binding by the antibody; and at least one agent that blocks non-specific binding of proteins or nucleic acids derived from a cell or embryo sample to the antibody (e.g., directly and/or indirectly). In some embodiments, the kit further comprises an antibody that specifically binds to a target nucleic acid or protein.

Additional embodiments are described herein.

DEFINITIONS

Figure 1A:
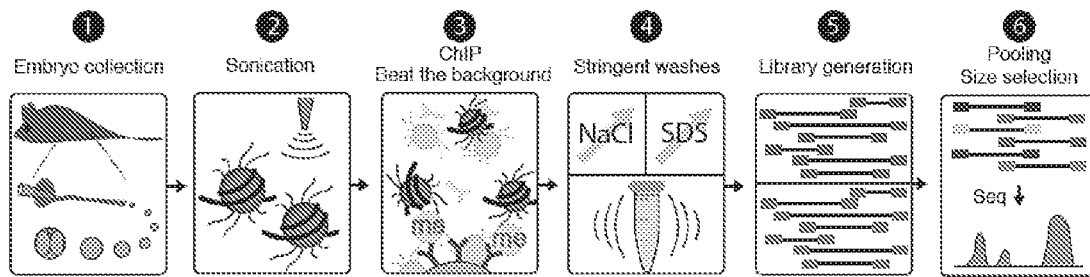
FIG. 1 shows development of µChIP-seq to investigate epigenomic landscapes in mouse embryos. a, Schematic overview of µChIP-seq strategy. Step 1 illustrates harvesting of in vivo-developed oocytes, 2-cell or 8-cell embryos flushed from mouse oviducts. Additional steps includes; blocking of unspecific binding using histone octameres and non-immunized IgGs to mimic the surface of ChIP-complexes (step 3) and optimizing stringency of washes to the affinity of the desired antibody (step 4). µChIP-seq libraries were pooled before size selection and purification to reduce loss and hence contribute to keep the number of PCR amplification cycles low (step 6). b, Genome browser snapshot of H3K4me3, H3K27ac, and Input µChIP-seq results in metaphase II oocytes, 2- and 8-cell embryos, and mouse ESCs. c-d, Confocal laser scanning micrographs showing H3K4me3 levels in (c) MII oocyte and (d) pronuclear (PN) stage PN2 and PN4 zygotes, 2-cell, 4-cell and 8-cell stage embryos reveal a sudden loss of H3K4me3 at the late 2-cell stage.

To facilitate an understanding of the present technology, a number of terms and phrases are defined below. Additional definitions are set forth throughout the detailed description.

A "subject" is an animal, such as a vertebrate, and preferably a mammal, such as a human. Mammals are understood to include, but are not limited to, murines, simians, humans, bovines, cervids, equines, porcines, canines, felines, etc.

As used herein, the term "host cell" refers to any eukaryotic or prokaryotic cell (e.g., bacterial cells such as E. coli, yeast cells, mammalian cells, avian cells, amphibian cells, plant cells, fish cells, and insect cells), whether located in vitro or in vivo. For example, host cells may be located in a transgenic animal.

As used herein, the term "prokaryotes" refers to a group of organisms that usually lack a cell nucleus or any other membrane-bound organelles. In some embodiments, prokaryotes are bacteria. The term "prokaryote" includes both archaea and eubacteria.

As used, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "cell culture" refers to any in vitro culture of cells. Included within this term are continuous cell lines (e.g., with an immortal phenotype), primary cell cultures, transformed cell lines, finite cell lines (e.g., non-transformed cells), and any other cell population maintained in vitro.

As used herein, a "nucleic acid" shall mean any nucleic acid molecule, including, without limitation, DNA, RNA, and hybrids thereof. The nucleic acid bases that form nucleic acid molecules can be the bases A, C, G, T and U, as well as derivatives thereof. Derivatives of these bases are well known in the art. The term should be understood to include, as equivalents, analogs of either DNA or RNA made from nucleotide analogs. The term as used herein also encompasses cDNA, that is complementary, or copy, DNA produced from an RNA template, for example by the action of a reverse transcriptase.

As used herein, "nucleic acid sequencing data", "nucleic acid sequencing information", "nucleic acid sequence", "genomic sequence", "genetic sequence", "fragment sequence", or "nucleic acid sequencing read" denotes any information or data that is indicative of the order of the nucleotide bases (e.g., adenine, guanine, cytosine, and thymine/uracil) in a molecule (e.g., a whole genome, a whole transcriptome, an exome, oligonucleotide, polynucleotide, fragment, etc.) of DNA or RNA.

It should be understood that the present teachings contemplate sequence information obtained using all available varieties of techniques, platforms or technologies, including, but not limited to: capillary electrophoresis, microarrays, ligation-based systems, polymerase-based systems, hybridization-based systems, direct or indirect nucleotide identification systems, pyrosequencing, ion- or pH-based detection systems, electronic signature-based systems, etc.

Reference to a base, a nucleotide, or to another molecule may be in the singular or plural. That is, "a base" may refer to a single molecule of that base or to a plurality of the base, e.g., in a solution.

A "polynucleotide", "nucleic acid", or "oligonucleotide" refers to a linear polymer of nucleosides (including deoxyribonucleosides, ribonucleosides, or analogs thereof) joined by internucleosidic linkages. Typically, a polynucleotide comprises at least three nucleosides. Usually oligonucleotides range in size from a few monomeric units, e.g. 3-4, to several hundreds of monomeric units. Whenever a polynucleotide such as an oligonucleotide is represented by a sequence of letters, such as "ATGCCTG," it will be understood that the nucleotides are in 5' to 3' order from left to right and that "A" denotes deoxyadenosine, "C" denotes deoxycytidine, "G" denotes deoxyguanosine, and "T" denotes thymidine, unless otherwise noted. The letters A, C, G, and T may be used to refer to the bases themselves, to nucleosides, or to nucleotides comprising the bases, as is standard in the art.

As used herein, the term "library" refers to a plurality of nucleic acids, e.g., a plurality of different nucleic acids.

As used herein the term, "in vitro" refers to an artificial environment and to processes or reactions that occur within an artificial environment. In vitro environments include, but are not limited to, test tubes and cell cultures. The term "in vivo" refers to the natural environment (e.g., an animal or a cell) and to processes or reaction that occur within a natural environment.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include cells, tissues, embryos, and blood products, such as plasma, serum and the like. Such examples are not however to be construed as limiting the sample types applicable to the present invention.

DETAILED DESCRIPTION

In some embodiments, the present invention provides chromatin immunoprecipitation (ChIP) methods. In particular, the present invention provides methods and compositions for performing ChIP (e.g., ChIP-seq) assays on small numbers or cells.

The invention overcomes a long-standing problem in the fields of genome regulation and epigenetics to be able to study, in cell types available only in limited numbers, the genomic location of DNA binding proteins such as transcription factors and histone proteins with regulatory and epigenetic chemical modifications. Chromatin immunoprecipitation and high throughput sequencing (ChIP-seq) is a powerful method to study where specific proteins are bound in a genome. Conventional ChIP-seq is however hampered by the need of large numbers of cells, typically millions of cells, therefore not allowing for the study of cells available only in limited numbers.

Rotem (Single-cell ChIP-seq reveals cell subpopulations defined by chromatin state. Nature biotechnology 33.11 (2015): 1165) describes a drop-based microfluidic device used to decipher chromatin data at single cell resolution. However, this drop-based microfluidic device has several limitations; it is not easily available due to high cost and expertises in interdisciplinary fields are required. Not only does the system require thousands of barcoded cells to start with, but also yields a limited number of valid sequencing reads (on average 1000 reads) per single cell and 50% of the reads are unspecific. When taking into account that this number of reads is obtained when targeting a histone mark that is present at more than 20,000 sites in the genome, the information obtained from each single cell is very limited. This makes it incredibly challenging to differentiate between single-cell variation and technical artifacts. Additionally, this strategy requires a large number of cells to be sequenced in order to evaluate intercellular variability.

Standard ChIP assays involve the steps of: DNA and associated proteins on chromatin in living cells or tissues are cross-linked; The DNA-protein complexes (chromatin-protein) are then sheared into smaller fragments (e.g., 10,000 to 50 (e.g., 10,000, 5000, 1000, 500, 250, 100, or 50) bp DNA fragments by sonication or nuclease digestion; and cross-linked DNA fragments associated with the protein(s) of interest are selectively immunoprecipitated from the cell lysate using an appropriate protein-specific antibody.

The biggest challenge when scaling down ChIP-seq from millions of cells to only a few hundred cells is to be able to still distinguish the signal from the background noise. If simply just scaling down all factors using conventional methods one will not get any signal that can be distinguished from the noise. Experiments described herein determined that the noise observed in ChIP-seq comes from the immunoprecipitation step. When fragmented DNA and the bound proteins (chromatin) are incubated with magnetic beads coupled to specific antibodies, antibody target proteins with associated DNA are bound, but importantly unspecific binding also takes place resulting in the co-precipitation of DNA sequences not associated with the target protein. This noise introduced by unspecific binding becomes highly significant and problematic when scaling down the cell number used for ChIP-seq. It was contemplated that because an excess of antibodies is used when binding these to magnetic beads, most or all of the surface available to biological macromolecules are i) the surface of the antibodies themselves and after some time of incubation with cell lysate/chromatin ii) the specifically captured chromatin pieces and iii) unspecifically bound macromolecules that bind to i) or ii). Each of i) ii) and iii) provides surface that may allow for unspecific binding.

Experiments described herein demonstrated that the noise introduced by unspecific binding can be competed out. Chromatin largely consists of histone proteins organized as octameres with DNA wrapped around them. In some embodiments, absent in silico filtering of known, introduced sequences, it may be problematic to introduce DNA into an assay where high throughput sequencing is used for readout, and it would be problematic if the histone proteins in the octameres or nucleosomes contained the same chemical posttranslational modifications as they do in vivo because these are often the targets of ChIP antibodies. Therefore, in some embodiments, one or more blocking agents such as recombinant histone H2A, H2B, H3 and H4 proteins without chemical modifications that are assembled by these in vitro as octameres are utilized as agents to reduce non-specific binding. These synthesized octameres mimic the surface of their in vivo counterparts. In some embodiments, to mimic the surface of the specific antibodies themselves, non-immunized IgG antibodies, non-reactive antibodies of the same isotype as the specific antibody used for ChIP-seq are utilized. In some embodiments, both the histone octamers and non-immunized antibodies or antibodies immunized to a target that is not present in the sample (e.g., Rabbit Anti-Mouse IgG H&L (ab46540)) are used. In some embodiments, histones/octameres with posttranslational modifications are used (e.g., when the specific antibody used for ChIP targets a non-histone protein, e.g. a transcription factor).

It is contemplated that by using an excess of synthetic octameres and/or non-immunized IgGs bind to sites of biological macromolecules before these macromolecules get a chance to interact with the antibody coated magnetic beads or free antibodies. Furthermore, synthetic octameres and non-immunized IgGs bind up and block the availability to sites of unspecific interaction on antibodies, magnetic beads and the specifically captured chromatin complexes. In some embodiments, the blocking agent is provided at a concentration of 0.01 μg to 10 μg (e.g., 1 μg).

Further experiments described herein demonstrated that it was possible to compete out the noise from the unspecific binding, with the result that most of the DNA captured on the magnetic beads came from sites of specific interaction of the protein of interest. Thus, most of the DNA that was purified, prepared and sequenced provided specific signals. This is important for gaining a high signal-to-noise ratio and high quality ChIP-seq data.

The current disclosure provides systems and methods that overcome limitations of prior methods. Accordingly, provided herein is a highly sensitive ChIP-seq method that allows for the study of a small number (e.g., 1000,000 or less to a few hundred or less or a single cell or cell fraction or lysate (e.g., of a single cell or embryo) cells to reveal where specific targets are bound throughout a genome. This allows the study of homogenously purified in vivo cell types such as e.g., hippocampus cells from the brain of a single mouse, cancer stem cells and subpopulations of cancer cells, oocytes and cells of the early mammalian embryo.

For example, in some embodiments, the present invention provides a method of performing immunoprecipitation (e.g., ChIP) and high throughput sequencing (ChIP-seq), comprising: a) treating (e.g., sonicating, chemically treating, or enzymatically treating (e.g., with MNase or DNase) a sample comprising a plurality of cells, tissue, biopsy samples, or embryos under conditions such that chromatin in the cells is fragmented; b) contacting the sample with an epitope binding factor (e.g., antibody) that specifically binds to a target molecule (e.g., protein or nucleic acid), wherein the antibody is free or bound to a solid support; c) contacting the sample with at least one agent that blocks non-specific binding of proteins or nucleic acids from the sample to the antibody; d) washing the sample under stringent conditions; e) generating sequencing libraries; and f) pooling the sequencing libraries. In some embodiments, the at least one agent is histones (e.g., monomers, dimers, tetramers, or octameres), non-immunized IgGs, IgGs immunized to a target that is not present in the sample, e.g. Rabbit Anti-Mouse IgG H&L (ab46540) or a combination thereof. In some embodiments, the method further comprises the step of performing a sequencing assay with the pooled sequencing library.

In some embodiments, the sample of cells is 1,000,000 or less (e.g., 1,000,000, 500,000, 100,000, 50,000, 25,000, 10,000, 5000, 1000, 900, 800, 700, 600, 500, 400, 300, 200, 100, 50, 25, 10, 5, or less) cells or embryos. In some embodiments, the sample is 10 (e.g., 9, 8, 7, 6, 5, 4, 3, 2, or a single) cell or embryo or the lysate or fraction of a single cell or embryo. In some embodiments, the embryo is a 2 cell embryo, a 4 cell embryo, or an 8 cell embryo.

In some embodiments, the solid support is magnetic or paramagnetic beads, agarose beads, or sepharose beads. In some embodiments, the target molecule is a protein (e.g., transcription factor or histone (e.g., H3K4me3, H3, or K27ac), DNA binding protein, RNA binding protein, or chromatin binding protein), enzymatically or chemically added marker (e.g., label), or nucleic acid. In some embodiments, the histone is cross-linked (e.g., with formaldehyde, UV, etc.) or native (e.g., not crosslinked).

Further embodiments provide kits comprising one or more reagents for performing ChIP-seq. In some embodiments, kits comprise one or more blocking agents, along with additional optional components (e.g., antibodies, buffers, solid supports, controls, ect.).

The DNA associated with the complex is then purified and identified by polymerase chain reaction (PCR), microarrays (ChIP-on-chip), molecular cloning and sequencing, or direct high-throughput sequencing (ChIP-Seq). See e.g., below for exemplary sequencing methods). Exemplary chromatin sources, crosslinking and fragmenting methods are described below.

In some embodiments, the method comprises identification of a protein and posttranslational modification of a protein associated with a target chromatin. Generally, chromatin refers to the combination of nucleic acids and proteins in the nucleus of a eukaryotic cell. However, it is contemplated that the term "chromatin" may also refer to the combination of any nucleic acid sequence and proteins associated with the nucleic acid sequence in any cell.

The present invention is not limited to a particular cell type. Examples include, but are not limited to, cells in culture, stem cells (e.g., cancer stem cells), primary cells in culture, oocytes, etc. In some embodiments, the compositions and methods described herein find use in the analysis of embryos (e.g., 2, 4, or 8 cell embryos).

Chromatin may comprise single stranded nucleic acid, double stranded nucleic acid, or a combination thereof. In some embodiments, chromatin comprises single stranded nucleic acid. In other embodiments, chromatin comprises a combination of single stranded and double stranded nucleic acids. In yet other embodiments, chromatin comprises double stranded nucleic acid.

Chromatin may comprise a ribonucleic acid (RNA), a deoxyribonucleic acid (DNA), or a combination of RNA and DNA. In some embodiments, chromatin comprises a combination of a RNA sequence and proteins associated with the RNA sequence in a cell. Non-limiting examples of RNA sequences may include mRNA, and non-coding RNA such as tRNA, rRNA, snoRNAs, microRNAs, siRNAs, piRNAs and the long noncoding RNA (lncRNA). In preferred embodiments, chromatin comprises a combination of a DNA sequence and proteins associated with the DNA sequence in a cell. In other embodiments, chromatin comprises a combination of RNA and DNA sequences, and proteins associated with the RNA and DNA sequence in a cell. Non limiting examples of chromatin that may comprise a combination of RNA and DNA may include genomic DNA undergoing transcription, or genomic DNA comprising non-coding RNA such as lncRNA.

The chromatin may be genomic chromatin such as, chromatin from a chromosome of a cell, or chromatin from an organelle in the cell. Alternatively, chromatin may be chromatin from an extrachromosomal nucleic acid sequence. In some embodiments, the chromatin is chromatin from an organelle in the cell. Non-limiting examples of chromatin from an organelle may include mitochondrial nucleic acid sequence in plant and animal cells, and a chloroplast nucleic acid sequence in plant cells. In some embodiments, the nucleic acid is a mitochondrial nucleic acid sequence. In other embodiments, the nucleic acid sequence is a chloroplast nucleic acid sequence.

In some embodiments, chromatin is chromatin from an extrachromosomal nucleic acid sequence. The term "extrachromosomal," as used herein, refers to any nucleic acid sequence not contained within the cell's genomic nucleic acid sequence. An extrachromosomal nucleic acid sequence may comprise some sequences that are identical or similar to genomic sequences in the cell, however, an extrachromosomal nucleic acid sequence as used herein does not integrate with genomic sequences of the cell. Non-limiting examples of an extrachromosomal nucleic acid sequence may include a plasmid, a virus, a cosmid, a phasmid, and a plasmid.

The primary protein components of genomic eukaryotic chromatin are histones that compact the DNA into a nucleosome. The nucleosome comprises an octamere of histone proteins around which is wound a stretch of double stranded DNA sequence of about 150 to about 250 bp in length. Histones H2A, H2B, H3 and H4 are part of the nucleosome while histone H1 may act to link adjacent nucleosomes together into a higher order structure. Histones are subject to post translational modifications which may affect their function in regulating chromatin function. Such modifications may include methylation, citrullination, acetylation, phosphorylation, SUMOylation, ubiquitination, and ADP-ribosylation.

Many further polypeptides and protein complexes interact with the nucleosome and the histones to regulate chromatin function. A "polypeptide complex" as used herein, is intended to describe proteins and polypeptides that assemble together to form a unitary association of factors. The members of a polypeptide complex may interact with each other via non-covalent or covalent bonds. Typically members of a polypeptide complex will cooperate to enable binding either to a nucleic acid sequence or to polypeptides and proteins already associated with or bound to a nucleic acid sequence in chromatin. Chromatin associated polypeptide complexes may comprise a plurality of proteins and/or polypeptides which each serve to interact with other polypeptides that may be permanently associated with the complex or which may associate transiently, dependent upon cellular conditions and position within the cell cycle. Hence, particular polypeptide complexes may vary in their constituent members at different stages of development, in response to varying physiological conditions or as a factor of the cell cycle. By way of example, in animals, polypeptide complexes with known chromatin remodelling activities include Polycomb group gene silencing complexes as well as Tritho-rax group gene activating complexes.

In some embodiments, chromatin is fragmented. Any method of fragmenting chromatin known in the art may be used. Such methods may include physical methods of fragmenting chromatin, or enzymatic digestion of a nucleic acid sequence of a chromatin. In some embodiments, a fragment of chromatin may be generated using enzymatic digestion of a nucleic acid sequence in chromatin. Non-limiting examples of enzymatic digestion may include random or sequence specific enzymatic digestion using restriction enzymes, nucleases, combinations of restriction enzymes and nucleases, or combinations of nicking and other nucleases such as NEBNext fragmentase, which comprises a nicking enzyme that randomly generates nicks in double stranded DNA and another enzyme that cuts the strand opposite to the generated nicks.

In other embodiments, a fragment of chromatin may be generated using a physical method of fragmenting the chromatin. Non-limiting examples of physical fragmenting methods that may be used to fragment chromatin may include nebulization, sonication, and hydrodynamic shearing. In some embodiments, a fragment of chromatin may be generated using nebulization. In other embodiments, a fragment of chromatin may be generated using hydrodynamic shearing. In preferred embodiments, a fragment of chromatin may be generated using sonication. During sonication, a sample comprising chromatin is subjected to ultrasonic waves, whose vibrations produce gaseous cavitations in the liquid that shear or break high molecular weight molecules such as chromatin through resonance vibration. Sonication methods that may be used to generate chromatin are known in the art. A fragment of chromatin may comprise a nucleic acid sequence fragment and may be about 10, 50, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950, 3000, 4000, 5000, 6000, 7000, 8000, 9000, or about 10000 bases long or more. In some embodiments, chromatin may comprise a nucleic acid sequence fragment of about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or about 500 bases long. In other embodiments, chromatin may comprise a nucleic acid sequence fragment of about 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or about 1000 bases long. In yet other embodiments, chromatin may comprise a nucleic acid sequence fragment of about 1000, 1010, 1020, 1030, 1040, 1050, 1060, 1070, 1080, 1090, 1100, 1110, 1120, 1130, 1140, 1150, 1160, 1170, 1180, 1190, 1200, 1210, 1220, 1230, 1240, 1250, 1260, 1270, 1280, 1290, 1300, 1310, 1320, 1330, 1340, 1350, 1360, 1370, 1380, 1390, 1400, 1410, 1420, 1430, 1440, 1450, 1460, 1470, 1480, 1490, or about 1500 bases long. In other embodiments, chromatin may comprise a nucleic acid sequence fragment of about 1500, 1510, 1520, 1530, 1540, 1550, 1560, 1570, 1580, 1590, 1600, 1610, 1620, 1630, 1640, 1650, 1660, 1670, 1680, 1690, 1700, 1710, 1720, 1730, 1740, 1750, 1760, 1770, 1780, 1790, 1800, 1810, 1820, 1830, 1840, 1850, 1860, 1870, 1880, 1890, 1900, 1910, 1920, 1930, 1940, 1950, 1960, 1970, 1980, 1990, or about 2000 bases long. In additional embodiments, chromatin may comprise a nucleic acid sequence fragment of about 2000, 2100, 2150, 2200, 2250, 2300, 2350, 2400, 2450, or about 2500 bases long. In other embodiments, chromatin may comprise a nucleic acid sequence fragment of about 2000, 2050, 2100, 2150, 2200, 2250, 2300, 2350, 2400, 2450, or about 2500 bases long. In still other embodiments, chromatin may comprise a nucleic acid sequence fragment of about 2500, 2550, 2600, 2650, 2700, 2750, 2800, 2850, 2900, 2950, 3000, 4000, 5000, 6000, 7000, 8000, 9000, or about 10000 bases long or more.

In some embodiments, a complex of proteins with a nucleic acid may be preserved by crosslinking protein and nucleic acid complexes in a chromatin prior to lysing a cell and isolating the chromatin. In other embodiments, histones are native. Crosslinking is the process of joining two or more molecules such as two proteins or a protein and a nucleic acid molecule, by a covalent bond. Molecules may be cross-linked by irradiation with ultraviolet light, or by using chemical crosslinking reagents. Chemical crosslinking reagents capable of crosslinking proteins and nucleic acids are known in the art and may include crosslinking reagents that target amines, sulfhydryls, carboxyls, carbonyls or hydroxyls; homobifunctional or heterobifunctional crosslinking reagent, variable spacer arm length or zero-length crosslinking reagents, cleavable or non-cleavable crosslinking reagents, and photoreactive crosslinking reagents. Non-limiting examples of crosslinking reagents that may be used to crosslink protein complexes and/or protein complexes and nucleic acids may include formaldehyde, glutaraldehyde, disuccinimidyl glutarate, disuccinimidyl suberate, a photoreactive amino acid such as photo-leucine or photo-methionine, and succinimidyl-diazirine. The degree of crosslinking can and will vary depending on the application of a method of the invention, and may be experimentally determined.

In some embodiments, a complex of proteins with a nucleic acid in chromatin is preserved by crosslinking protein and nucleic acid complexes in a cell prior to lysing using formaldehyde. In an exemplary embodiment, a complex of proteins with a nucleic acid in chromatin is preserved by crosslinking protein and nucleic acid complexes in a cell prior to lysing using formaldehyde.

A skilled practitioner of the art will appreciate that protocols for lysing a cell can and will vary depending on the type of cell, the target chromatin of the invention, and the specific application of a method of the invention. Non limiting examples of methods that may be used to lyse a cell may include cell lysis using a detergent, an enzyme such as lysozyme, incubation in a hypotonic buffer which causes a cell to swell and burst, mechanical disruption such as liquid homogenization by forcing a cell through a narrow space, sonication, freeze/thaw, mortar and pestle, glass beads, and combinations thereof.

Buffer conditions used during lysing and isolation of chromatin can and will be altered to control stringent conditions during cell lysis and isolation to preserve association of proteins and nucleic acid sequences of a chromatin. "Stringent conditions" in the context of chromatin isolation are conditions capable of preserving specific association of proteins and nucleic acids of a chromatin, but minimizing non-specific association of proteins and nucleic acids. Stringent condition can and will vary depending on the application of a method of the invention, the target chromatin of the invention, the nucleic acid sequence in a target chromatin, the proteins or protein complexes associated with a target chromatin of the invention, whether or not proteins, protein complexes and nucleic acid sequences are cross-linked, and the conditions used for crosslinking proteins, protein complexes and nucleic acid sequences of a target chromatin. For instance, more stringent buffer conditions may be used in a method of the invention wherein proteins, protein-protein complexes, and protein-nucleic acid complexes are cross-linked compared to a method of the invention wherein proteins, protein-protein complexes, and protein-nucleic acid complexes are not crosslinked. As such, stringent buffer conditions used during cell lysis and isolation of a nucleic acid sequence of the invention may be experimentally determined for each application wherein a method of the invention is used. Buffer conditions that may alter stringent conditions during cell lysis and isolation may include pH, salt, and detergent concentrations. In preferred embodiments, proteins, protein-protein complexes, and protein-nucleic acid complexes of a target chromatin of the invention are cross-linked, and stringent buffer conditions are used during lysis and isolation of chromatin and during capture/immuneprecipitation and wash steps.

In some embodiments, the agent for cross-linking is formaldehyde or UV light. In some embodiments, the cross-linked chromatin is sheared by sonication, providing fragments of 10-10.00 base pairs (bp) (e.g., see above) in length.

In some embodiments, cell debris in the sheared lysate is then cleared by sedimentation and protein-DNA complexes are selectively immunoprecipitated using specific antibodies to the protein(s) of interest. In some embodiments, the antibodies are coupled to agarose, sepharose or magnetic beads. The immunoprecipitated complexes (e.g., the bead-antibody-protein-target DNA sequence complex) are then collected and washed to remove non-specifically bound chromatin, in some embodiments, the protein-DNA cross-link is reversed and proteins are removed by digestion with proteinase (e.g., proteinase K, Qiagen protease, etc.).

Particular sequencing technologies contemplated by the technology are next-generation sequencing (NGS) methods that share the common feature of massively parallel, high-throughput strategies, with the goal of lower costs in comparison to older sequencing methods (see, e.g., Voelkerding et al., Clinical Chem., 55: 641-658, 2009; MacLean et al., Nature Rev. Microbiol., 7: 287-296; each herein incorporated by reference in their entirety). NGS methods can be broadly divided into those that typically use template amplification and those that do not. Amplification-requiring methods include pyrosequencing commercialized by Roche as the 454 technology platforms (e.g., GS 20 and GS FLX), the Solexa platform commercialized by Illumina, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences and emerging platforms commercialized by VisiGen, Oxford Nanopore Technologies Ltd., Life Technologies/Ion Torrent, and Pacific Biosciences, respectively.

In pyrosequencing (Voelkerding et al., Clinical Chem., 55: 641-658, 2009; MacLean et al., Nature Rev. Microbiol., 7: 287-296; U.S. Pat. Nos. 6,210,891; 6,258,568; each herein incorporated by reference in its entirety), the NGS fragment library is clonally amplified in-situ by capturing single template molecules with beads bearing oligonucleotides complementary to the adapters. Each bead bearing a single template type is compartmentalized into a water-in-oil microvesicle, and the template is clonally amplified using a technique referred to as emulsion PCR. The emulsion is disrupted after amplification and beads are deposited into individual wells of a picotitre plate functioning as a flow cell during the sequencing reactions. Ordered, iterative introduction of each of the four dNTP reagents occurs in the flow cell in the presence of sequencing enzymes and a luminescent reporter such as luciferase. In the event that an appropriate dNTP is added to the 3' end of the sequencing primer, the resulting production of ATP causes a burst of luminescence within the well, which is recorded using a CCD camera. It is possible to achieve read lengths greater than or equal to 400 bases, and $10^6$ sequence reads can be achieved, resulting in up to 500 million base pairs (Mb) of sequence.

In the Solexa/Illumina platform (Voelkerding et al., Clinical Chem., 55: 641-658, 2009; MacLean et al., Nature Rev. Microbiol., 7: 287-296; U.S. Pat. Nos. 6,833,246; 7,115,400; 6,969,488; each herein incorporated by reference in its entirety), sequencing data are produced in the form of shorter-length reads. In this method, the fragments or amplicons of the NGS library are captured on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure on the surface of the flow cell. These loops of DNA are denatured and cleaved. Forward strands are then sequenced with reversible dye terminators. The sequence of incorporated nucleotides is determined by detection of post-incorporation fluorescence, with each fluor and block removed prior to the next cycle of dNTP addition. Sequence read length ranges from 36 nucleotides to over 100 nucleotides, with overall output exceeding 1 billion nucleotide pairs per analytical run.

Sequencing nucleic acid molecules using SOLiD technology (Voelkerding et al., Clinical Chem., 55: 641-658, 2009; MacLean et al., Nature Rev. Microbiol., 7: 287-296; U.S. Pat. Nos. 5,912,148; 6,130,073; each herein incorporated by reference in their entirety) also involves clonal amplification of the NGS fragment library by emulsion PCR. Following this, beads bearing template are immobilized on a derivatized surface of a glass flow-cell, and a primer complementary to the adapter oligonucleotide is annealed. However, rather than utilizing this primer for 3' extension, it is instead used to provide a 5' phosphate group for ligation to interrogation probes containing two probe-specific bases followed by 6 degenerate bases and one of four fluorescent labels. In the SOLiD system, interrogation probes have 16 possible combinations of the two bases at the 3' end of each probe, and one of four fluors at the 5' end. Fluor color, and thus identity of each probe, corresponds to specified color-space coding schemes. Multiple rounds (usually 7) of probe annealing, ligation, and fluor detection are followed by denaturation, and then a second round of sequencing using a primer that is offset by one base relative to the initial primer. In this manner, the template sequence can be computationally re-constructed, and template bases are interrogated twice, resulting in increased accuracy. Sequence read length averages 35 nucleotides, and overall output exceeds 4 billion bases per sequencing run.

In certain embodiments, HeliScope by Helicos BioSciences is employed (Voelkerding et al., Clinical Chem., 55: 641-658, 2009; MacLean et al., Nature Rev. Microbiol., 7: 287-296; U.S. Pat. Nos. 7,169,560; 7,282,337; 7,482,120; 7,501,245; 6,818,395; 6,911,345; 7,501,245; each herein incorporated by reference in their entirety). HeliScope sequencing is achieved by addition of polymerase and serial addition of fluorescently-labeled dNTP reagents. Incorporation events result in a fluor signal corresponding to the dNTP, and signal is captured by a CCD camera before each round of dNTP addition. Sequence read length ranges from 25-50 nucleotides, with overall output exceeding 1 billion nucleotide pairs per analytical run.

In some embodiments, 454 sequencing by Roche is used (Margulies et al. (2005) Nature 437: 376-380). 454 sequencing involves two steps. In the first step, DNA is sheared into fragments of approximately 300-800 base pairs and the fragments are blunt ended. Oligonucleotide adapters are then ligated to the ends of the fragments. The adapters serve as primers for amplification and sequencing of the fragments. The fragments can be attached to DNA capture beads, e.g., streptavidin-coated beads using, e.g., an adapter that contains a 5'-biotin tag. The fragments attached to the beads are PCR amplified within droplets of an oil-water emulsion. The result is multiple copies of clonally amplified DNA fragments on each bead. In the second step, the beads are captured in wells (picoliter sized). Pyrosequencing is performed on each DNA fragment in parallel. Addition of one or more nucleotides generates a light signal that is recorded by a CCD camera in a sequencing instrument. The signal strength is proportional to the number of nucleotides incorporated. Pyrosequencing makes use of pyrophosphate (PPi) which is released upon nucleotide addition. PPi is converted to ATP by ATP sulfurylase in the presence of adenosine 5' phosphosulfate. Luciferase uses ATP to convert luciferin to oxyluciferin, and this reaction generates light that is detected and analyzed.

The Ion Torrent technology is a method of DNA sequencing based on the detection of hydrogen ions that are released during the polymerization of DNA (see, e.g., Science 327 (5970): 1190 (2010); U.S. Pat. Appl. Pub. Nos. 20090026082, 20090127589, 20100301398, 20100197507, 20100188073, and 20100137143, incorporated by reference in their entireties for all purposes). A microwell contains a fragment of the NGS library to be sequenced. Beneath the layer of microwells is a hypersensitive ISFET ion sensor. All layers are contained within a CMOS semiconductor chip, similar to that used in the electronics industry. When a dNTP is incorporated into the growing complementary strand a hydrogen ion is released, which triggers the ion sensor. If homopolymer repeats are present in the template sequence, multiple dNTP molecules will be incorporated in a single cycle. This leads to a corresponding number of released hydrogens and a proportionally higher electronic signal. This technology differs from other sequencing technologies in that no modified nucleotides or optics are used. The per-base accuracy of the Ion Torrent sequencer is ~99.6% for 50 base reads, with ~100 Mb generated per run. The read-length is 100 base pairs. The accuracy for homopolymer repeats of 5 repeats in length is ~98%. The benefits of ion semiconductor sequencing are rapid sequencing speed and low upfront and operating costs. However, the cost of acquiring a pH-mediated sequencer is approximately $50,000, excluding sample preparation equipment and a server for data analysis.

Another exemplary nucleic acid sequencing approach that may be adapted for use with the present technology was developed by Stratos Genomics, Inc. and involves the use of Xpandomers. This sequencing process typically includes providing a daughter strand produced by a template-directed synthesis. The daughter strand generally includes a plurality of subunits coupled in a sequence corresponding to a contiguous nucleotide sequence of all or a portion of a target nucleic acid in which the individual subunits comprise a tether, at least one probe or nucleobase residue, and at least one selectively cleavable bond. The selectively cleavable bond(s) is/are cleaved to yield an Xpandomer of a length longer than the plurality of the subunits of the daughter strand. The Xpandomer typically includes the tethers and reporter elements for parsing genetic information in a sequence corresponding to the contiguous nucleotide sequence of all or a portion of the target nucleic acid. Reporter elements of the Xpandomer are then detected. Additional details relating to Xpandomer-based approaches are described in, for example, U.S. Pat. Pub No. 20090035777, entitled "HIGH THROUGHPUT NUCLEIC ACID SEQUENCING BY EXPANSION," filed Jun. 19, 2008, which is incorporated herein in its entirety.

Other single molecule sequencing methods include real-time sequencing by synthesis using a VisiGen platform (Voelkerding et al., Clinical Chem., 55: 641-58, 2009; U.S. Pat. No. 7,329,492; U.S. patent application Ser. No. 11/671, 956; U.S. patent application Ser. No. 11/781,166; each herein incorporated by reference in their entirety) in which fragments of the NGS library are immobilized, primed, then subjected to strand extension using a fluorescently-modified polymerase and florescent acceptor molecules, resulting in detectible fluorescence resonance energy transfer (FRET) upon nucleotide addition.

Another real-time single molecule sequencing system developed by Pacific Biosciences (Voelkerding et al., Clinical Chem., 55: 641-658, 2009; MacLean et al., Nature Rev. Microbiol., 7: 287-296; U.S. Pat. Nos. 7,170,050; 7,302, 146; 7,313,308; 7,476,503; all of which are herein incorporated by reference) utilizes reaction wells 50-100 nm in diameter and encompassing a reaction volume of approximately 20 zeptoliters ($10^{-21}$ liters). Sequencing reactions are performed using immobilized template, modified phi29 DNA polymerase, and high local concentrations of fluorescently labeled dNTPs. High local concentrations and continuous reaction conditions allow incorporation events to be captured in real time by fluor signal detection using laser excitation, an optical waveguide, and a CCD camera.

In certain embodiments, single molecule real time (SMRT) DNA sequencing methods using zero-mode waveguides (ZMWs) developed by Pacific Biosciences, or similar methods, are employed. With this technology, DNA sequencing is performed on SMRT chips, each containing thousands of zero-mode waveguides (ZMWs). A ZMW is a hole, tens of nanometers in diameter, fabricated in a 100 nm metal film deposited on a silicon dioxide substrate. Each ZMW becomes a nanophotonic visualization chamber providing a detection volume of just 20 zeptoliters. At this volume, the activity of a single molecule can be detected amongst a background of thousands of labeled nucleotides. The ZMW provides a window for watching DNA polymerase as it performs sequencing by synthesis. Within each chamber, a single DNA polymerase molecule is attached to the bottom surface such that it permanently resides within the detection volume. Phospholinked nucleotides, each type labeled with a different colored fluorophore, are then introduced into the reaction solution at high concentrations that promote enzyme speed, accuracy, and processivity. Due to the small size of the ZMW, even at these high, biologically relevant concentrations, the detection volume is occupied by nucleotides only a small fraction of the time. In addition, visits to the detection volume are fast, lasting only a few microseconds, due to the very small distance that diffusion has to carry the nucleotides. The result is a very low background.

In some embodiments, nanopore sequencing is used (Soni G V and Meller A. (2007) Clin Chem 53: 1996-2001). A nanopore is a small hole, of the order of 1 nanometer in diameter. Immersion of a nanopore in a conducting fluid and application of a potential across it results in a slight electrical current due to conduction of ions through the nanopore. The amount of current that flows is sensitive to the size of the nanopore. As a DNA molecule passes through a nanopore, each nucleotide on the DNA molecule obstructs the nanopore to a different degree. Thus, the change in the current passing through the nanopore as the DNA molecule passes through the nanopore represents a reading of the DNA sequence.

In some embodiments, a sequencing technique uses a chemical-sensitive field effect transistor (chemFET) array to sequence DNA (for example, as described in US Patent Application Publication No. 20090026082). In one example of the technique, DNA molecules are placed into reaction chambers, and the template molecules are hybridized to a sequencing primer bound to a polymerase. Incorporation of one or more triphosphates into a new nucleic acid strand at the 3' end of the sequencing primer can be detected by a change in current by a chemFET. An array can have multiple chemFET sensors. In another example, single nucleic acids can be attached to beads, and the nucleic acids can be amplified on the bead, and the individual beads can be transferred to individual reaction chambers on a chemFET array, with each chamber having a chemFET sensor, and the nucleic acids can be sequenced.

In some embodiments, sequencing technique uses an electron microscope (Moudrianakis E. N. and Beer M. Proc Natl Acad Sci USA. 1965 March; 53:564-71). In one example of the technique, individual DNA molecules are labeled using metallic labels that are distinguishable using an electron microscope. These molecules are then stretched on a flat surface and imaged using an electron microscope to measure sequences.

In some embodiments, "four-color sequencing by synthesis using cleavable fluorescent nucleotide reversible terminators" as described in Turro, et al. PNAS 103: 19635-40 (2006) is used, e.g., as commercialized by Intelligent BioSystems. The technology described in U.S. Pat. Appl. Pub. Nos. 2010/0323350, 2010/0063743, 2010/0159531, 20100035253, 20100152050, incorporated herein by reference for all purposes.

Processes and systems for such real time sequencing that may be adapted for use with the technology are described in, for example, U.S. Pat. No. 7,405,281, entitled "Fluorescent nucleotide analogs and uses therefor", issued Jul. 29, 2008 to Xu et al.; U.S. Pat. No. 7,315,019, entitled "Arrays of optical confinements and uses thereof", issued Jan. 1, 2008 to Turner et al.; U.S. Pat. No. 7,313,308, entitled "Optical analysis of molecules", issued Dec. 25, 2007 to Turner et al.; U.S. Pat. No. 7,302,146, entitled "Apparatus and method for analysis of molecules", issued Nov. 27, 2007 to Turner et al.; and U.S. Pat. No. 7,170,050, entitled "Apparatus and methods for optical analysis of molecules", issued Jan. 30, 2007 to Turner et al.; and U.S. Pat. Pub. Nos. 20080212960, entitled "Methods and systems for simultaneous real-time monitoring of optical signals from multiple sources", filed Oct. 26, 2007 by Lundquist et al.; 20080206764, entitled "Flowcell system for single molecule detection", filed Oct. 26, 2007 by Williams et al.; 20080199932, entitled "Active surface coupled polymerases", filed Oct. 26, 2007 by Hanzel et al.; 20080199874, entitled "CONTROLLABLE STRAND SCISSION OF MINI CIRCLE DNA", filed Feb. 11, 2008 by Otto et al.; 20080176769, entitled "Articles having localized molecules disposed thereon and methods of producing same", filed Oct. 26, 2007 by Rank et al.; 20080176316, entitled "Mitigation of photodamage in analytical reactions", filed Oct. 31, 2007 by Eid et al.; 20080176241, entitled "Mitigation of photodamage in analytical reactions", filed Oct. 31, 2007 by Eid et al.; 20080165346, entitled "Methods and systems for simultaneous real-time monitoring of optical signals from multiple sources", filed Oct. 26, 2007 by Lundquist et al.; 20080160531, entitled "Uniform surfaces for hybrid material substrates and methods for making and using same", filed Oct. 31, 2007 by Korlach; 20080157005, entitled "Methods and systems for simultaneous real-time monitoring of optical signals from multiple sources", filed Oct. 26, 2007 by Lundquist et al.; 20080153100, entitled "Articles having localized molecules disposed thereon and methods of producing same", filed Oct. 31, 2007 by Rank et al.; 20080153095, entitled "CHARGE SWITCH NUCLEOTIDES", filed Oct. 26, 2007 by Williams et al.; 20080152281, entitled "Substrates, systems and methods for analyzing materials", filed Oct. 31, 2007 by Lundquist et al.; 20080152280, entitled "Substrates, systems and methods for analyzing materials", filed Oct. 31, 2007 by Lundquist et al.; 20080145278, entitled "Uniform surfaces for hybrid material substrates and methods for making and using same", filed Oct. 31, 2007 by Korlach; 20080128627, entitled "SUBSTRATES, SYSTEMS AND METHODS FOR ANALYZING MATERIALS", filed Aug. 31, 2007 by Lundquist et al.; 20080108082, entitled "Polymerase enzymes and reagents for enhanced nucleic acid sequencing", filed Oct. 22, 2007 by Rank et al.; 20080095488, entitled "SUBSTRATES FOR PERFORMING ANALYTICAL REACTIONS", filed Jun. 11, 2007 by Foquet et al.; 20080080059, entitled "MODULAR OPTICAL COMPONENTS AND SYSTEMS INCORPORATING SAME", filed Sep. 27, 2007 by Dixon et al.; 20080050747, entitled "Articles having localized molecules disposed thereon and methods of producing and using same", filed Aug. 14, 2007 by Korlach et al.; 20080032301, entitled "Articles having localized molecules disposed thereon and methods of producing same", filed Mar. 29, 2007 by Rank et al.; 20080030628, entitled "Methods and systems for simultaneous real-time monitoring of optical signals from multiple sources", filed Feb. 9, 2007 by Lundquist et al.; 20080009007, entitled "CONTROLLED INITIATION OF PRIMER EXTENSION", filed Jun. 15, 2007 by Lyle et al.; 20070238679, entitled "Articles having localized molecules disposed thereon and methods of producing same", filed Mar. 30, 2006 by Rank et al.; 20070231804, entitled "Methods, systems and compositions for monitoring enzyme activity and applications thereof", filed Mar. 31, 2006 by Korlach et al.; 20070206187, entitled "Methods and systems for simultaneous real-time monitoring of optical signals from multiple sources", filed Feb. 9, 2007 by Lundquist et al.; 20070196846, entitled "Polymerases for nucleotide analog incorporation", filed Dec. 21, 2006 by Hanzel et al.; 20070188750, entitled "Methods and systems for simultaneous real-time monitoring of optical signals from multiple sources", filed Jul. 7, 2006 by Lundquist et al.; 20070161017, entitled "MITIGATION OF PHOTODAMAGE IN ANALYTICAL REACTIONS", filed Dec. 1, 2006 by Eid et al.; 20070141598, entitled "Nucleotide Compositions and Uses Thereof", filed Nov. 3, 2006 by Turner et al.; 20070134128, entitled "Uniform surfaces for hybrid material substrate and methods for making and using same", filed Nov. 27, 2006 by Korlach; 20070128133, entitled "Mitigation of photodamage in analytical reactions", filed Dec. 2, 2005 by Eid et al.; 20070077564, entitled "Reactive surfaces, substrates and methods of producing same", filed Sep. 30, 2005 by Roitman et al.; 20070072196, entitled "Fluorescent nucleotide analogs and uses therefore", filed Sep. 29, 2005 by Xu et al; and 20070036511, entitled "Methods and systems for monitoring multiple optical signals from a single source", filed Aug. 11, 2005 by Lundquist et al.; and Korlach et al. (2008) "Selective aluminum passivation for targeted immobilization of single DNA polymerase molecules in zero-mode waveguide nanostructures" PNAS 105(4): 1176-81, all of which are herein incorporated by reference in their entireties.

In some embodiments, the present invention provides kits and systems for use in ChIP-SEQ. In some embodiments, kits and systems comprise one or more of an antibody that specifically binds to a target protein, wherein said antibody is bound to a solid support, at least one agent that blocks non-specific binding of proteins derived from a cell or embryo sample to the antibody, reagents for performing a stringent wash, or reagents for performing a sequencing assay.

The compositions and methods described herein find use in a variety of research, screening, and clinical applications. The compositions and methods find use in the fields of e.g. epigenetics, brain research, cancer research, stem cell research, induced pluripotency, pluripotency, embryo development, gametogenesis.

EXPERIMENTAL

Examples

Example 1

Materials and Methods

Collection of Oocytes and Preimplantation Embryos

Four- to eight-week-old donors were injected with 5 units of pregnant mare serum gonadotropin (PMS) (for oocytes/2-cells: 14.00, for 8-cells: 15.00, 100 µl of 50 I.U/ml solution) followed by 5 units of human chorionic gonadotropin (hCG) (for oocytes/2-cells: 11.00, For 8-cells: 15.00, 100 µl of 50 I.U/ml solution) 45/48 h post PMS. For 2-cells and 8-cells harvest, females were transferred to cages with males for breeding (immediately after hCG injections).

Oocyte collection. Donor mice were sacrificed by cervical dislocation 18 hours post hCG injection (no mating). Oviducts were transferred to a clean dish with M2 (Sigma) medium. The ampulla was identified under a stereomicroscope, and the oocytes released followed by removal of cumulus mass by room temperature incubation in M2 containing 0.3 mg/ml hyaluronidase. The oocytes were further washed in M2.

2-cell collection. Donor mice were sacrificed by cervical dislocation 45 hours post hCG injection/mating. Oviducts were transferred to a clean dish with M2 medium. Infundibulum was identified and the 2-cells were released by placing a syringe containing M2 inside the infundibulum opening, followed by flushing the M2 through the whole oviduct. The 2-cells were further washed in M2 medium.

8-cell collection. Donor mice were sacrificed by cervical dislocation 68 hours post hCG injection/mating. Oviducts were transferred to a clean dish with M2 medium. Infundibulum was identified and the 8-cells were released by placing a syringe containing M2 inside the infundibulum opening, followed flushing the M2 through the whole oviduct. The 8-cells were further washed in M2 medium.

Zona Removal

The oocytes/2-cells/8-cells were transferred to a 1504 drop of Acidic Thyrode's solution (Sigma), and further transferred to a drop of M2 immediately after the zona had been removed. 5 steps of washing in M2 were carried out, and the oocytes/2-cells/8-cells were ready for fixation.

Collection of Immature Oocytes from Prepubertal Mice

Immature oocytes were isolated from 12-day-old and 15-day-old prepubertal CD-1 mice (RjOrl:SWISS) as follows. Ovaries were removed with fine scissors and carefully freed from surrounding tissues with a 25G needle. Batches of five ovaries were placed in 800 µl DPBS in a 60 mm culture dish, 400 µl of Trypsin-EDTA (0.05%) (Gibco) was added immediately before fine mincing of the ovaries with a scalpel. After mincing, 5 µl of DNase I (10 U/µl) (Sigma, Cat. Nr. 04716728001) was added and the minced ovaries were incubated at 3TC for 20 minutes. Next, 20 µl of Colagenase Type II (100 mg/ml) (Sigma, Cat. Nr.C9407), 800 µl of DBPS and 400 µl of Trypsin-EDTA (0.05%) was added and the dish was incubated for 10 minutes at 37° C. Mechanical dissociation with a pipette then resulted in denuded oocytes. To remove any possible traces of somatic contaminants, and to remove the zona, oocytes were washed four times in M2 medium, incubated in two consecutive drops of M2 containing 0.3 mg/ml hyaluronidase, washed two times in M2 medium, then in two drops of Acidic Thyrode's solution (Sigma) and again washed four times in M2 medium. Batches of oocytes to be analyzed for DNA methylation were washed once in WGBS lysis solution (20 mM Tris-HCl, 20 mM KCl, 2 mM EDTA), transferred in a volume of maximum 5 µl to a 1.5 ml tube, snap frozen in liquid nitrogen and stored at −80° C. before further processing. Batches of oocytes for ChIP-seq was treated as described below.

ChIP-Seq

Cross-linking of oocytes, 2-cell or 8-cell embryos. Embryos were added to 50 µl M2 medium in a 0.6 ml tube and allowed to settle to the bottom. The volume was controlled by eye by comparing to another 0.6 ml tube with 50 µl M2 medium and adjusted with mouth pipette to 50 µl. 50 µl of PBS with 2% formaldehyde was added to get 1% final concentration and the sampled was vortexed carefully. The sample was incubated at room temperature for 8 minutes, and vortexed once more. To this, 12 µl of 1.25 M glycine stock (final concentration 125 mM) was added, the sample was mixed by gentle vortexing, incubated for 5 min at room temperature, and the vortexing was repeated once during the incubation step. The sample was centrifuge at 700 g for 10 min at 4° C. in a swinging-bucket rotor with soft deceleration settings and washed two times with 400 µl ice cold PBS. After the last wash, 10 µl was left and the sample was snap frozen in liquid nitrogen and stored at −80° C. As many pools of embryos as required for downstream ChIP-seq experiments are collected.

Binding of Antibodies to paramagnetic beads. The stock of paramagnetic Dynabeads® Protein A is vortexed thoroughly to ensure the suspension is homogenous before pipetting. 100 µl of Dynabeads® stock solution was transferred into a 1.5-ml tube, the tube was placed in a magnetic rack and beads were captured on the tube wall. The wash buffer is discarded, beads are washed two times in 500 µl of RIPA buffer (10 mM Tris-HCl pH 8.0, 140 mM NaCl, 1 mM EDTA, 0.5 mM EGTA, 1% Triton X-100, 0.1% SDS, 0.1% Na-deoxycholate) and resuspended in RIPA buffer to a final volume of 100 µl. 90 µL of RIPA buffer is aliquoted into a 200-µL PCR tubes on ice, vortexed thoroughly, and 2 µL of bead suspension is added to each of the 200 µL PCR tubes and 2 µl of either antibody to H3K4me3 (Merck Millipore, catalogue number 04-745) or to H3K27ac (Active Motif, catalogue number AM39133) is added to each tube. The sample is incubated at 40 rpm on a "head-over-tail" tube rotator for at least 4 hours at 4° C.

Chromatin Preparation. A desired number of cross-linked and frozen pools of embryos are removed from −80° C. and placed on dry-ice in an insulated box. For example four tubes with a total number of 500 2-cell embryos. Ten more minutes of cross-linking while thawing is performed as follows: One tube at the time is moved from dry-ice to ice for 5 seconds, and any frozen droplets are quickly pelleted by a brief spin with a mini-centrifuge. 100 µl of 1.1% formaldehyde solution (PBS with 1 mM EDTA, 1.1% formaldehyde, 20 mM sodium butyrate, 1 mM PMSF and protease inhibitor cocktail) is added and the sample is incubated for 10 minutes at room temperature and vortexed gently two times. Seven µl of 2.5 M glycine is added, the sample is vortexed gently and then incubated for 5 minutes before moving the tube to ice. The sample is centrifuged at 750 g for 10 min at 4° C. in a swinging-bucket rotor with soft deceleration settings. The sample is then washed two times with 400 µl PBS with 1 mM EDTA, 20 mM sodium butyrate, 1 mM PMSF and protease inhibitor cocktail. Ten µl is left after the last wash. For four tubes, a total of 120 µl of 0.8% SDS lysis buffer with 20 mM sodium butyrate, 1 mM PMSF and protease inhibitor cocktail was used. The first 60 µl is used, and then 2×30 µl for two consecutive rounds of washing through the four tubes by pipetting. The same tip is used and the entire volume (160 µl) is left in the last of the four tubes. Sample are then sonicateed 5×30 seconds using a UP100H Ultrasonic Processor (Hielscher) fitted with a 2 mm probe with 30 seconds pauses on ice between each 30 seconds session, using pulse settings with 0.5 second cycles and 27% power. 170 µl RIPA Dilution buffer (10 mM Tris-HCl pH 8.0, 175 mM NaCl, 1 mM EDTA, 0.625 mM EGTA, 1.25% Triton X-100, 0.125% Na-deoxycholate, 20 mM sodium butyrate, 1 mM PMSF and protease inhibitor cocktail) is added and the sample is centrifuged at 12,000 g in a swing-bucket for 10 minutes at 4° C. and then the supernatant is transferred to a 1.5 ml tube. 200 µl of RIPA Dilution buffer was added to the pellet and sonicated 3×30 seconds. The sample was centrifuged at 12,000 g in a swing-bucket for 8 min. The supernatant was removed and mixed well with the first supernatant, resulting in a total volume of about 530 µl of ChIP-ready chromatin.

Immunoprecipitation and Washes. Pre-incubated antibody-bead complexes were washed two times in 130 µl RIPA buffer by vortexing roughly. Samples were centrifuged in a minicentrifuge to bring down any solution trapped in the lid and capture antibody-bead complexes in a magnetic rack cooled on ice. 250 µl chromatin was added to each of anti H3K4me3 or H3K27ac reactions, and 25 µl was kept for input control. Two µl of cross-linked or non-cross-linked recombinant histone octameres and 1.25 ug of non-immunized rabbit IgG or an IgG that is immunized to a target not in the sample was added to ChIP reactions. IgG (Abcam, Rabbit Anti-Mouse IgG H&L, Cat No: ab46540) and recombinant histone ocatmeres (EpiCypher, Cat. No.:16-0001) were purchased from the listed vendors. Samples were incubated at 4° C., 40 rpm on a "head-over-tail" rotator for 30 hours. Chromatin-antibody-bead complexes were washed four times 100 µL ice-cold RIPA buffer. The concentration of SDS and NaCl was titrated for each antibody to find optimal conditions for maximized signal-to-noise ratio. For H3K4me3, samples were washed in 1×RIPA buffer with 0.2% SDS and 300 mM NaCl, 1×RIPA buffer with 0.23% SDS and 300 mM NaCl followed by 2×RIPA buffer with 0.2% SDS and 300 mM NaCl. For H3K27ac, samples were washed 4×RIPA buffer with 0.1% SDS and 140 mM NaCl. Each wash involved rough vortexing on full speed, and repeated twice with pauses on ice in between. Next wash 1×100 µl TE and carry out tube shift as previously described (Wang et al., supra; Shen et al., supra).

DNA Isolation and Purification. TE was removed and 150 µl ChIP elution buffer (20 mM Tris-HCl pH 7.5, 50 mM NaCl, 5 mM EDTA. 1% SDS, 30 ug RNase A) was added, the sample was incubated at 37 C, 1 hour at 1200 rpm on a Thermomixer. One µl of Proteinase K (20 mg/ml stock) was added to each tube and incubated at 68° C., 4 hours at 1250 rpm. Eluate was transferred to a 1.5 ml tube and a second elution was performed with 150 µl and pooled with the first supernatant. ChIP DNA was purified by phenol-chloroform isoamylalcohol extraction, ethanol-precipitated with 10 ml acrylamide carrier as described previously (Wang, L. et al. Programming and Inheritance of Parental DNA Methylomes in Mammals. Cell 157, 979-991 (2014); Shen, L. et al. Tet3 and DNA Replication Mediate Demethylation of Both the Maternal and Paternal Genomes in Mouse Zygotes. Cell Stem Cell 15, 459-470 (2014)) and dissolved in 10 WEB (10 mM Tris-HCl).

Library preparation and sequencing. Chip and input library preparation and was carried out according to the THRUPlex (Rubicon Genomics) procedure with some modifications including increased incubation times during library purification and size selection. Twelve ChIP libraries were pooled prior to AMPure XP purification and allowed to bind for 10 minutes after extensive mixing. Increased elution time, thorough mixing the use of a strong neodymium bar magnet allowed for elution in 25 µl EB. Sequencing procedures were carried out as described previously according to Illumina protocols with minor modifications (Illumina, San Diego, Calif.). All P12, P15, oocyte, 2-cell, and 8-cell ChIP-seq libraries were sequenced as paired-end and all NCCIT ChIP-seq libraries as single-end. Paired-end and single-end during sequencing of mESCs ChIP-seq libraries were combined. Single-end and paired-end library information for all samples have been deposited in the GEO database (GSE72784).

Sequence Read Alignment

Single- and paired-end µChIP-seq reads from H3K27ac and H3K4me3 experiments were aligned to the mm10 reference genome by using BWA-mem. For human ChIP-seq samples performed with human NCCIT cells, reads were aligned to the hg19 reference genome using BWA-mem. Unmapped and non-uniquely mapped reads were removed. PCR duplicate reads were removed with Picard. H3K4me3 ChIP-seq data for heart, liver, and cerebellum were downloaded from the mouse ENCODE project. H3K4me3 ChIP-seq data for sperm was downloaded from GEO database under accession number GSE42629 (Smith, Z. D. et al. DNA methylation dynamics of the human preimplantation embryo. Nature 511, 611-615 (2014)).

Results

Figure 1B:
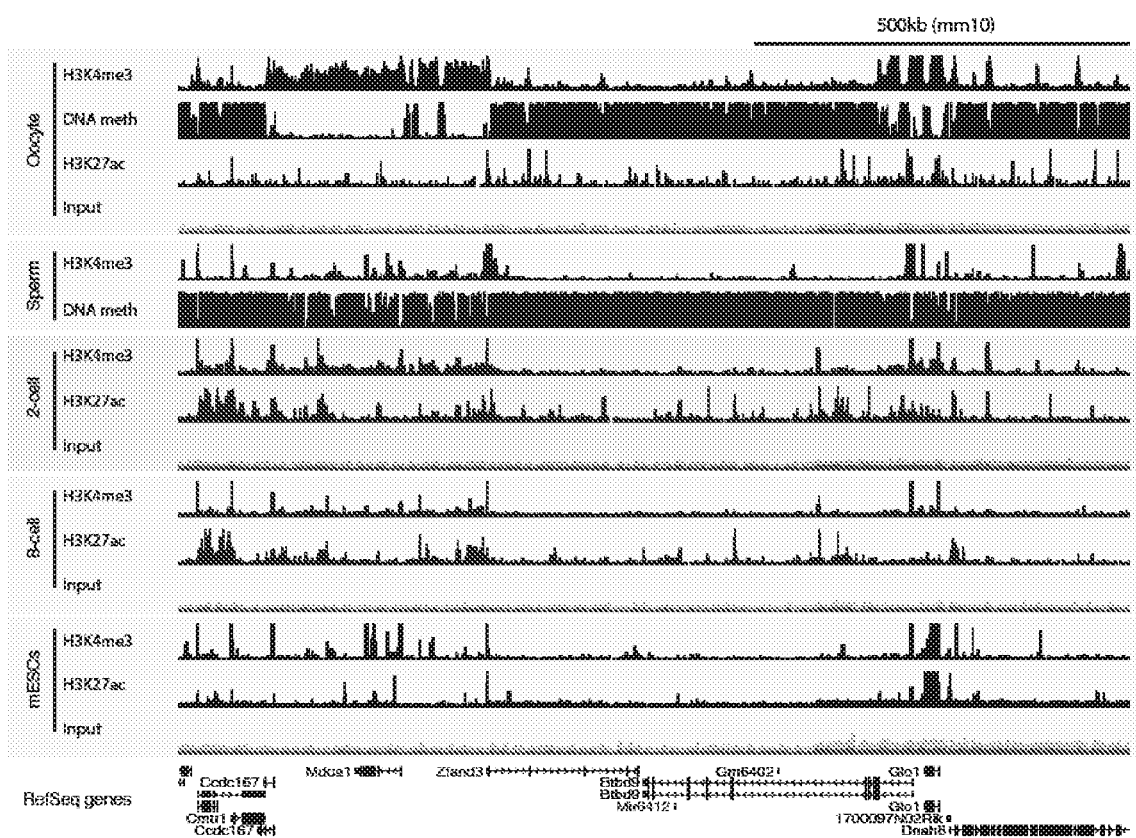
Figure 1C:
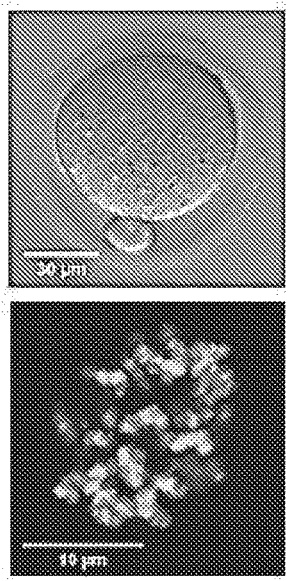
Figure 1D:
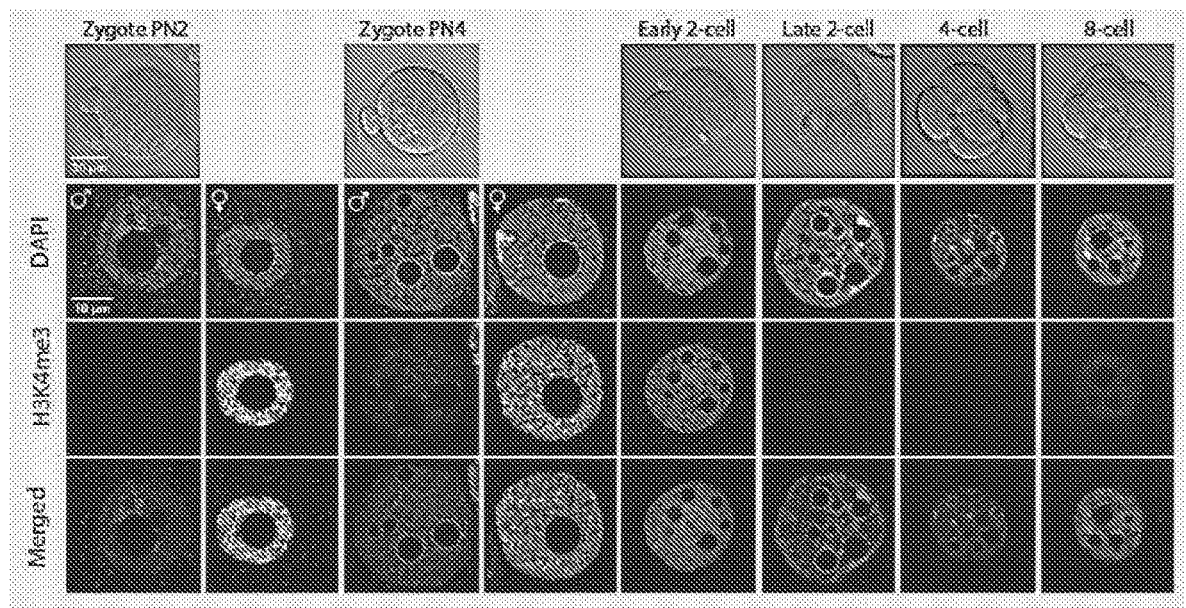
Figure 2A:
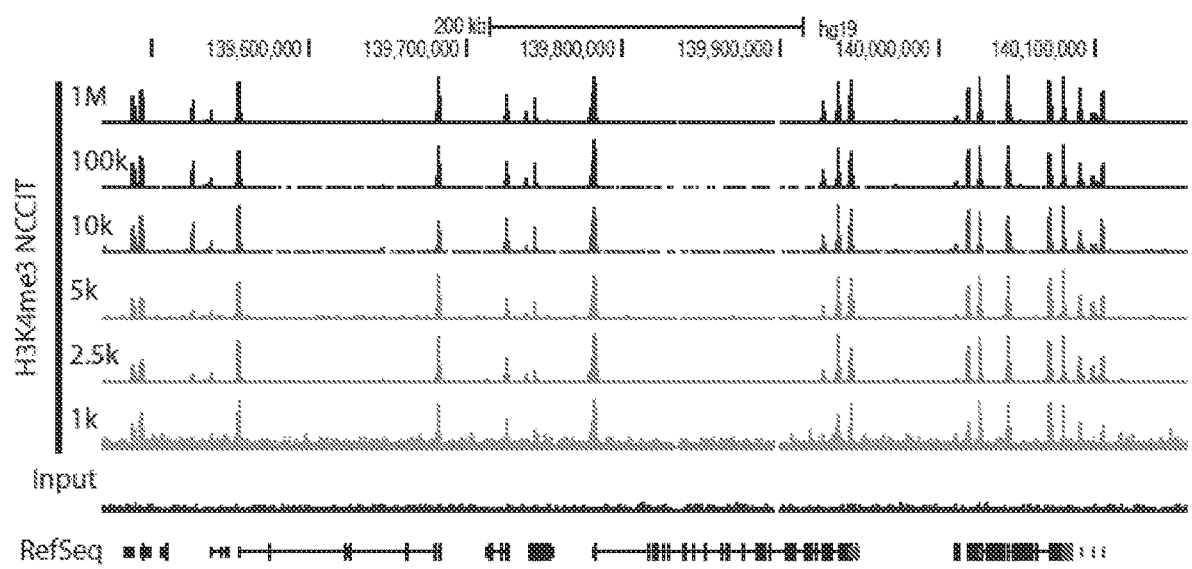
FIG. 2 shows µChIP-seq in human NCCIT cells and mouse embryonic stem cells. a, Genome browser snapshot for H3K4me3 µChIP-seq with different number of human NCCIT cells. b, The percentage of overlapping H3K4me3 peaks between top 10,000 H3K4me3 peaks detected from multiple µChIP-seq experiments with different numbers of cells. c, A genome browser snapshot for H3K27ac and H3K4me3 µChIP-seq in mouse ES cells. d, The percentage of overlapping H3K4me3 peaks between top 10,000 H3K4me3 peaks when comparing multiple µChIP-seq experiments performed with different numbers of cells. e, The percentage of overlapping H3K27ac peaks between multiple experiments using different numbers of cells. f, A scatter plot comparing RPKM values obtained from 1K cell µChIP-seq and ENCODE ChIP-seq results using an H3K4me3 antibody. g, ROC plots for H3K4me3 peaks identified from multiple μChIP-seq experiments. h, Boxplots of GC content comparing 500-cell H3K4me3 ChIP-seq detected and undetected ENCODE H3K4me3 peaks (KS-test p=0.81). i, Boxplots of ENCODE H3K4me3 signal comparing 500-cell H3K4me3 ChIP-seq detected and undetected H3K4me3 peaks (KS-test $p<2.2^{-16}$).
Figure 2B:
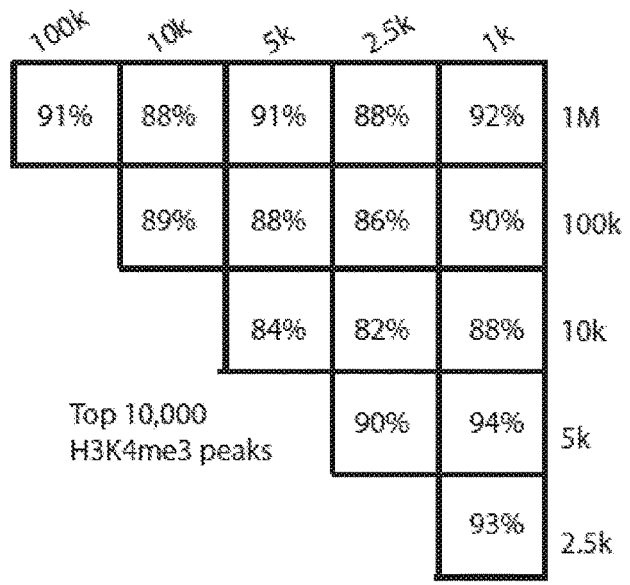
Figure 2C:
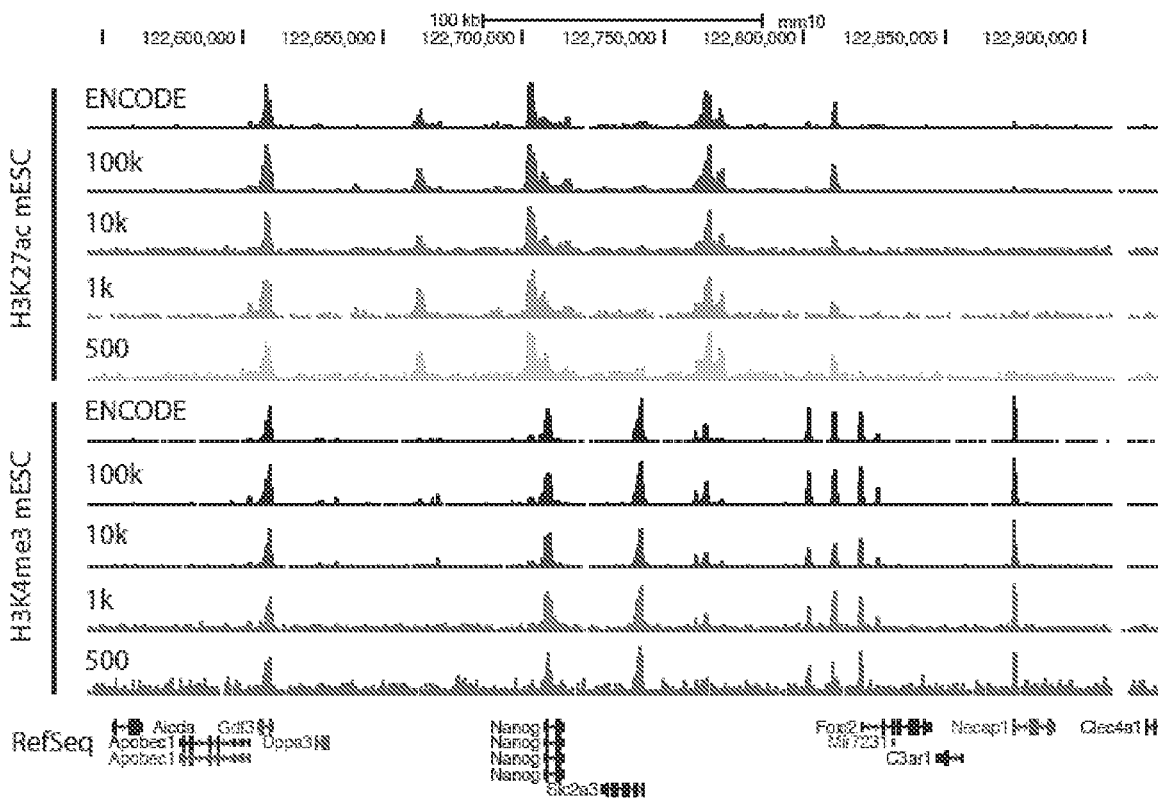
Figure 2D:
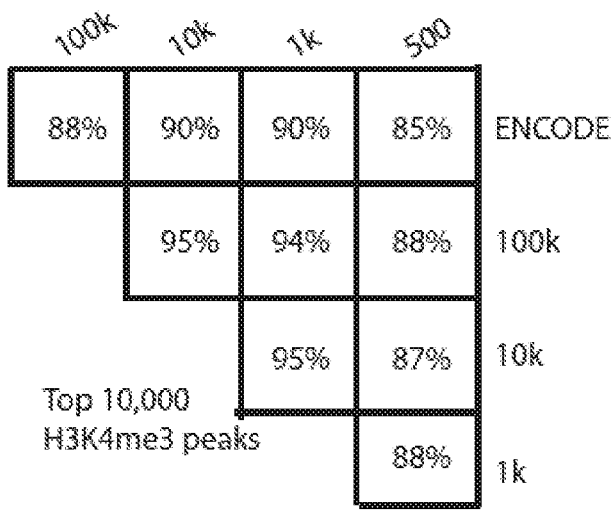
Figure 2E:
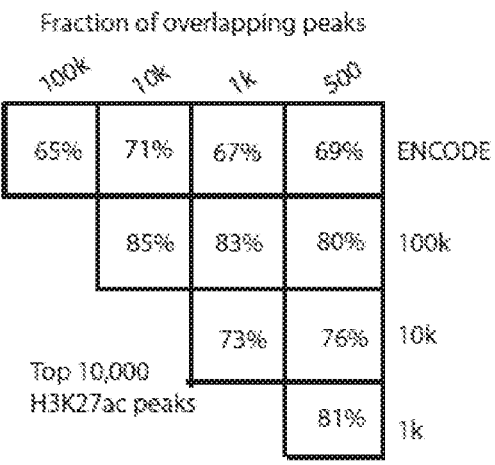
Figure 2E:
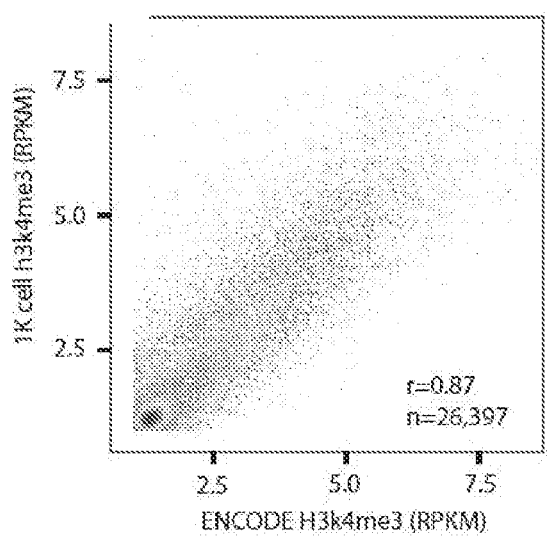
Figure 2G:
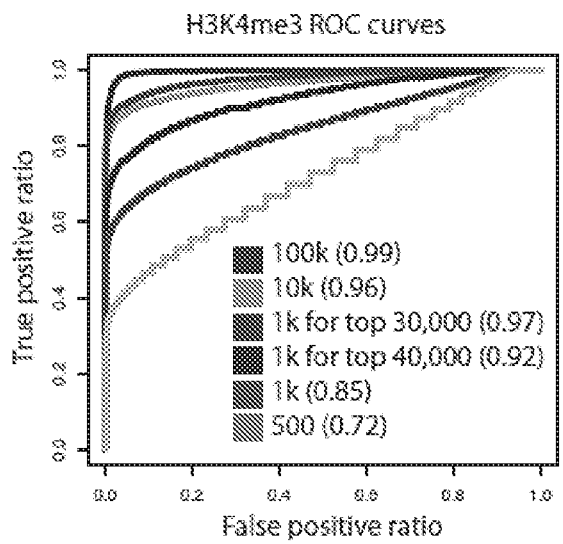
Figure 2H:
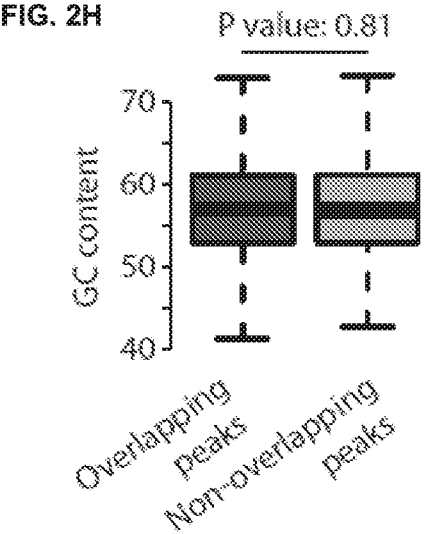
Figure 2I:
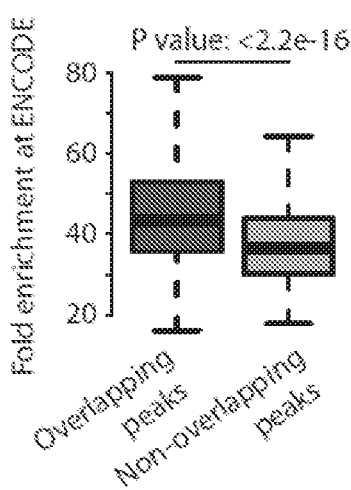
Figure 3A:
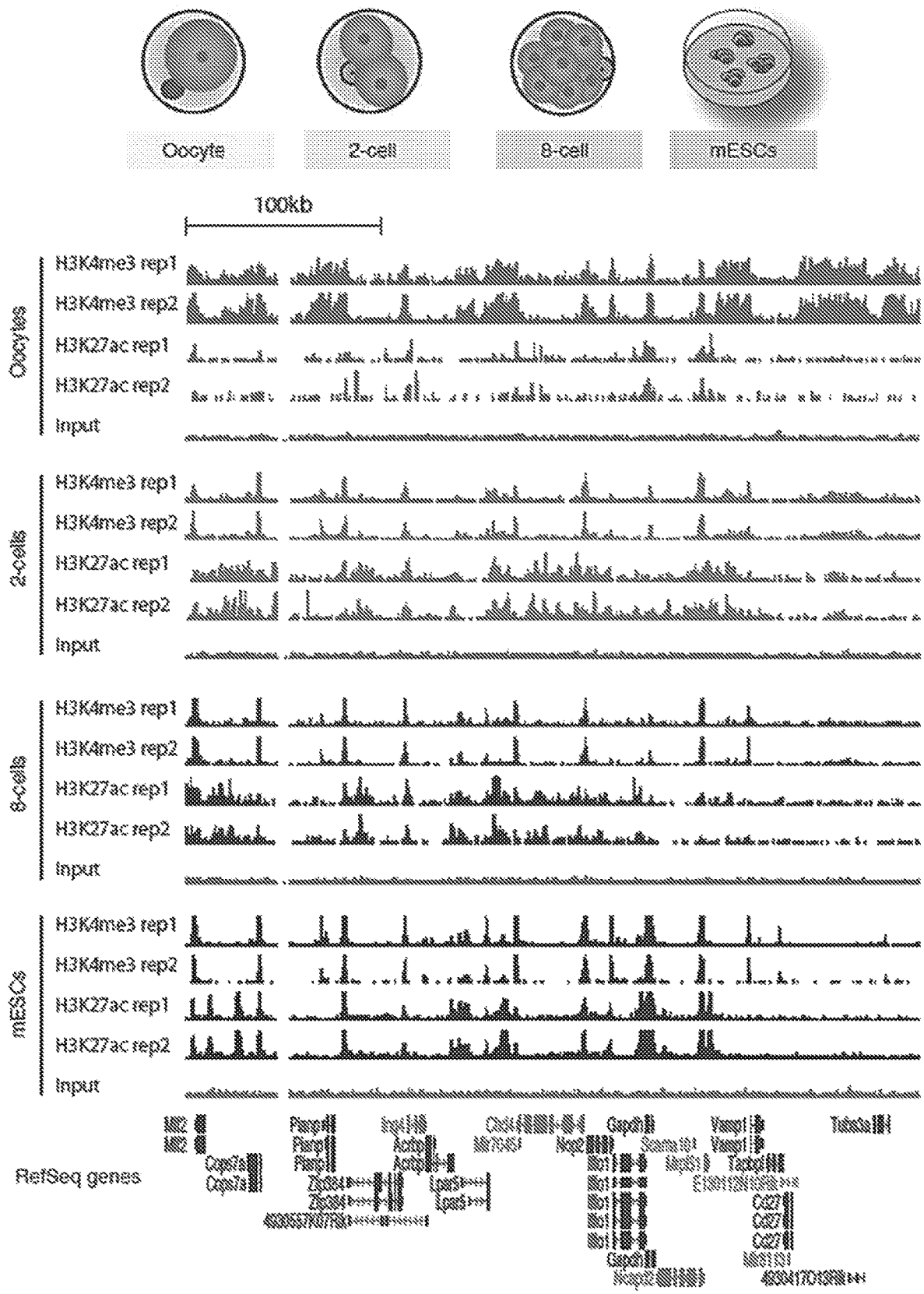
FIG. 3 shows reproducibility of μChIP-seq experiments. a, Genome browser snapshots of H3K4me3 and H3K27ac μChIP-seq results at metaphase II oocytes, 2- and 8-cell embryos and ESCs. b, Genome browser snapshots of H3K4me3 μChIP-seq results from P12, P15 and MII oocytes. c, Bar plots show the Pearson correlation coefficient between two biological replicates.
Figure 3B:
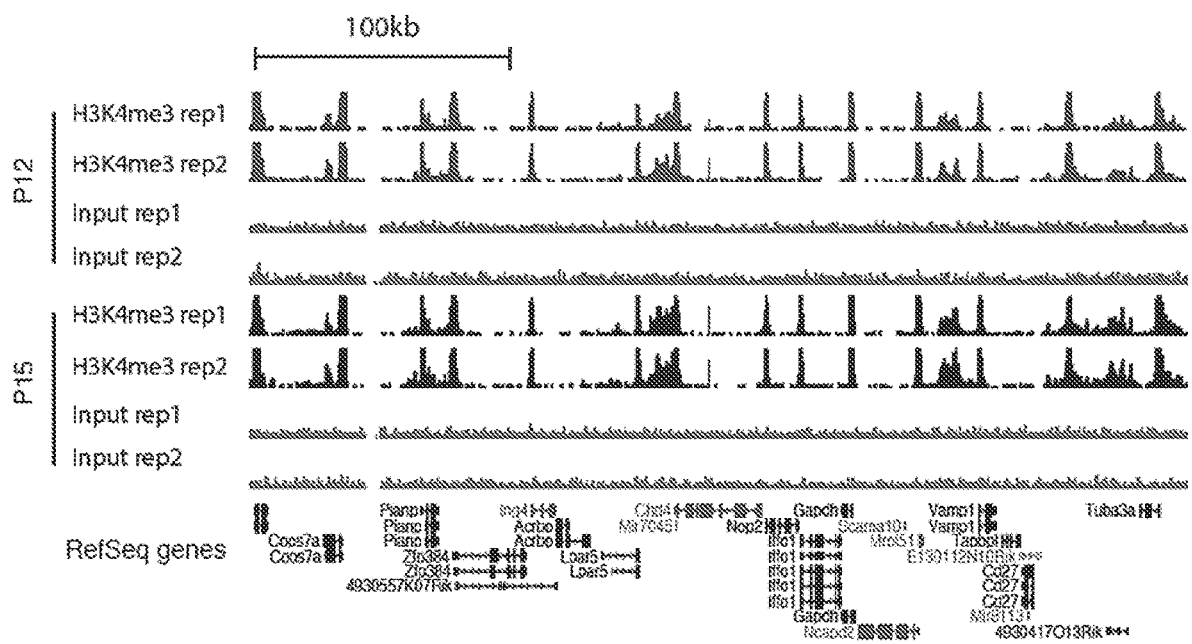
Figure 3C:
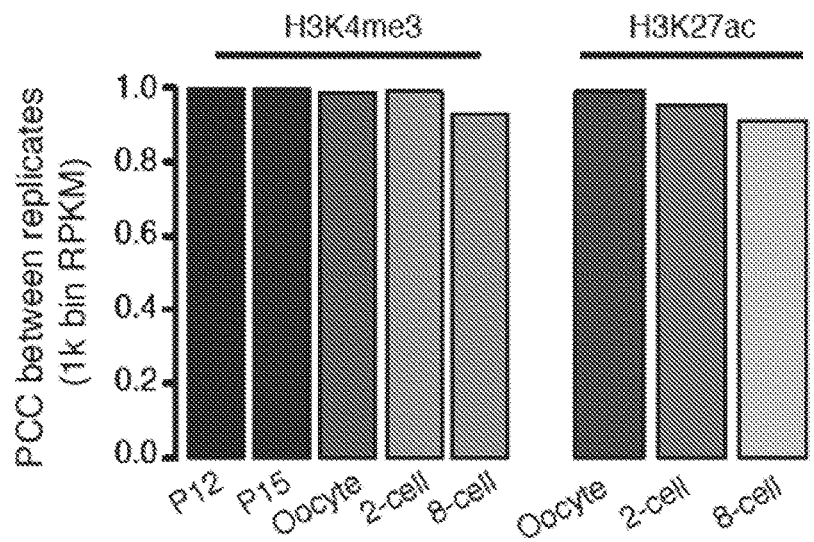

State of the art Chromatin immunoprecipitation coupled with high-throughput sequencing technology (ChIP-seq) can use as little as 500 cell-equivalents of chromatin per reaction but need 10,000 cells for initial steps (Lara-Astiaso, D. et al. Immunogenetics. Chromatin state dynamics during blood formation. Science 345, 943-949 (2014)), or require a highly specialized microfluidics device that is not readily available (Shen, J. et al. H3K4me3 epigenomic landscape derived from ChIP-Seq of 1 000 mouse early embryonic cells. Cell Res 25, 143-147 (2014)). To study histone modifications in early post-implantation embryos or oocytes, a highly sensitive micro-scale (µ)ChIP-seq method (FIG. 1a) was developed by optimizing multiple steps of ChIP and DNA sequencing library construction. µChIP-seq was validated in human embryonal carcinoma (NCCIT) cells (FIG. 2a, b) and mouse embryonic stem (ES) cells (FIG. 2c-g) for H3K4me3 and H3K27ac using a starting cell population with numbers ranging from 500 to 100,000. Notably, one can reliably detect 85% of ENCODE H3K4me3 peaks from as few as 500 cells (FIG. 2d). There was no GC bias between undetected and detected ENCODE H3K4me3 peaks (FIG. 2h); rather, the undetected peaks were weak ENCODE peaks (FIG. 2i). Applying μChIP-seq to 1,000 cells allowed detection of 90% of ENCODE peaks and 94% of peaks from large scale ChIP from the same ES cell culture batch (FIG. 2d). ChIP-seq was used to generate genome-wide H3K4me3 and H3K27ac histone modification maps from mouse oocytes, 2-cell and 8-cell stage embryos as well as ES cells (FIG. 1b) with two biological replicates (Table 1). Genome-wide histone modification maps showed high reproducibility between replicates (FIG. 3a-c). Because in vitro culture is known to affect the transcriptome and morphological and biochemical characteristics of mammalian embryos (Kues, W. A. et al. Genome-wide expression profiling reveals distinct clusters of transcriptional regulation during bovine preimplantation development in vivo. *Proc. Natl. Acad. Sci. U.S.A.* 105, 19768-19773 (2008)), in vivo developed embryos were used. A distinct architecture of H3K4me3 in oocytes in comparison to other cell types (FIG. 1b) was observed. In line with ChIP-seq results, immunofluorescence staining of H3K4me3 shows high levels of H3K4me3 in the oocyte and the H3K4me3 signals are rapidly lost from the early to the late 2-cell stage embryo (FIG. 1c, d).

Figure 4:
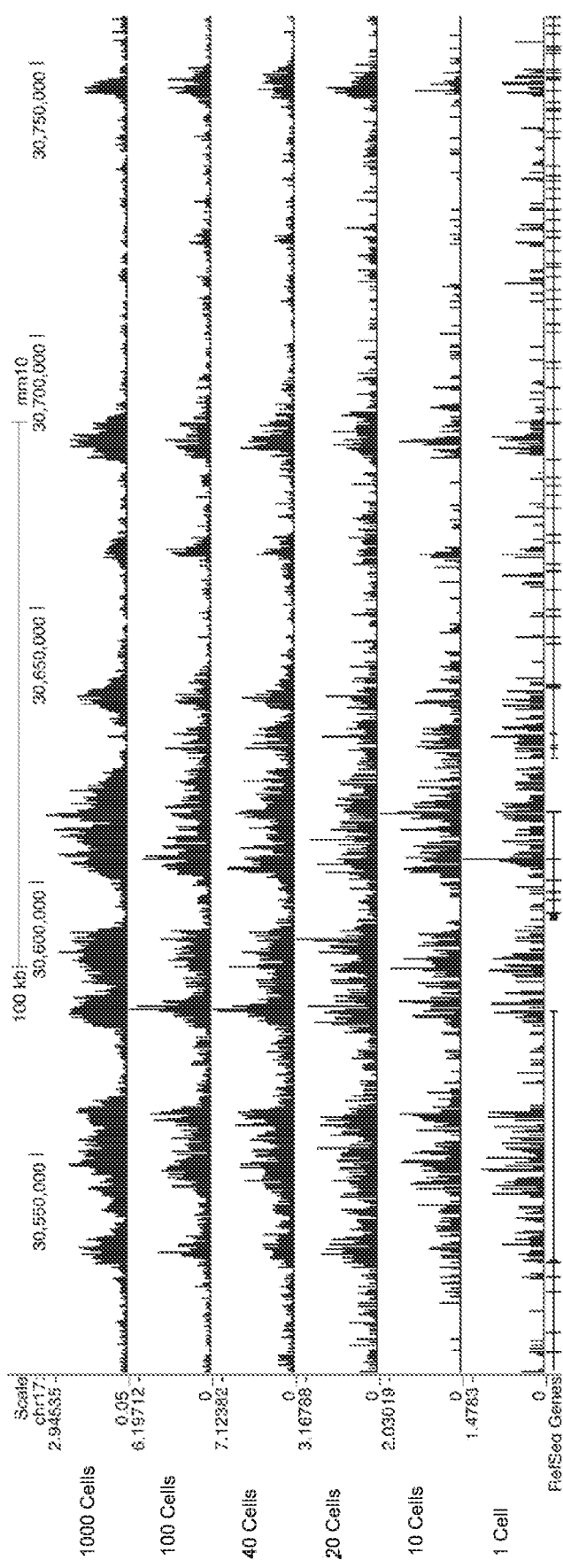
FIG. 4 shows low cell number ChIP-seq and single-cell ChIP-seq results.
Figure 5:
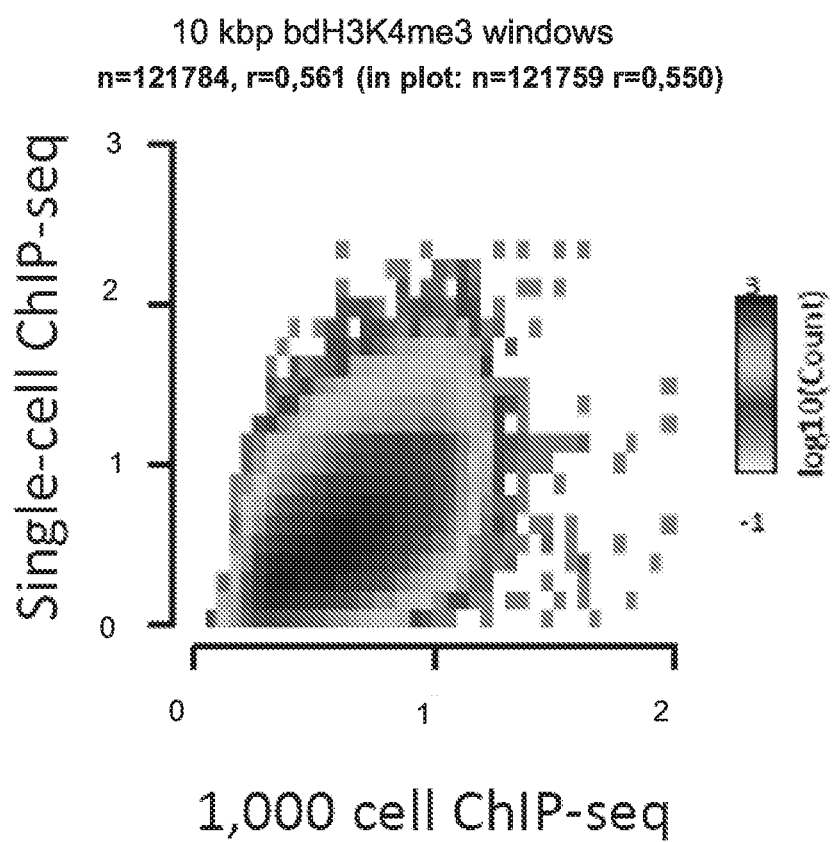
FIG. 5 shows single-cell ChIP-seq results.

FIGS. 4 and 5 show ChIP-seq results from low and single cell samples.

Example 2

Alternative Procedure for Low Cell Number ChIP-Seq and Single-Cell ChIP-Seq

This Example describes an alternate procedure for low cell number ChIP-seq. Purified pools of cells or single cells are placed in a drop of medium or PBS in a cell culture dish or well or similar device and handled under a microscope. Cell(s) are transferred to a drop containing, for example, 1% formaldehyde for cross-linking. Alternatively, ChIP is carried out without doing cross-linking, or with the use of another cross-linking reagent. The sample is incubated at room temperature for 8 minutes. Cell(s) are then transferred to a drop containing glycine (final concentration 125 mM) and incubated for 5 min at room temperature. Cells are washed two to four times by transferring cell(s) to two to four drops containing PBS. Cell(s) are transferred to a clean tube, for example a 0.6 ml tube and snap frozen in liquid nitrogen and stored at −80° C. or subjected to cell lysis without freezing.

Lysis and chromatin Preparation. Cross-linked and frozen cell(s) are placed on dry-ice in an insulated box. Tube(s) are transferred to ice and lysis buffer is added. To 10 μl of cell(s) in PBS, 150 μl of SDS lysis buffer with 20 mM sodium butyrate, 1 mM PMSF and protease inhibitor cocktail is added (final SDS concentration is in the range of 0.05% to 2%). Sonicate e.g. 2×30 seconds using a UP100H Ultrasonic Processor (Hielscher) fitted with a 2 mm probe. Sonication is adjusted to cell number, volume skill of operator and other variables. Thirty seconds pauses on ice between each 30 seconds session, using pulse settings with 0.5 second cycles and 27% power are used. 170 μl RIPA Dilution buffer (10 mM Tris-HCl pH 8.0, 175 mM NaCl, 1 mM EDTA, 0.625 mM EGTA, 1.25% Triton X-100, 0.125% Na-deoxycholate, 20 mM sodium butyrate, 1 mM PMSF and protease inhibitor cocktail) is added and cells are centrifuged at 12,000 g in a swing-bucket for 10 minutes at 4° C. The supernatant is transferred to a 0.6 ml tube. 200 μl of RIPA Dilution buffer is added to the pellet the resulting solution is sonicated 2×30 seconds, followed by centrifugation at 12,000 g in a swing-bucket for 8 min. The supernatant is removed and mixed well with the first supernatant, resulting in a total volume of about 530 μl of ChIP-ready chromatin. One may also just do one round of sonication and avoid the centrifugation step, and instead move directly onwards with dilution of chromatin in RIPA buffer to a final SDS concentration that is favorable to the antibody and epitope in question for the experiment (e.g., 0.1% SDS). This may help to reduce loss.

Immunoprecipitation and Washes using pre-incubated antibody-bead complexes. Alternatively, unbound antibody can be added directly to the chromatin/cell lysate, incubated and then Protein A beads added for capture of chromatin. Pre-incubated antibody-bead complexes are washed two times in 130 μl RIPA buffer by vortexing roughly. Tubes are centrifuged in a minicentrifuge to bring down any solution trapped in the lid and capture antibody-bead complexes in a magnetic rack. Chromatin is added to each tube containing antibody-bead coplexes. Alternatively, the antibody-bead complexes are added to the tube containing the chromatin from one or more cells. This last strategy may help reducing loss. 0.1-2 ul of Protein A or Protein G paramagnetic beads (or other suitable surface) are used per reaction. One 1 ul of Protein A beads is a good starting point. Beads are prepared as described under Example 1 with an incubation of 30 minutes to 48 hours using an antibody of choice.

0.1 μg of cross-linked or non-cross-linked recombinant histone octameres (this reagent may be added in a higher or lower amount, e.g. 0.01 μg to 10 μg), and 0.25 ug of non-immunized IgG or an IgG that is immunized to a target not in the sample are added to ChIP reactions (this reagent may be added in a higher or lower amount, e.g. 0.01 μg to 10 μg). One may e.g. use IgG (Abcam, Rabbit Anti-Mouse IgG H&L, Cat No: ab46540) and recombinant histone ocatmeres (EpiCypher, Cat. No.:16-0001). The samples are incubate at 4° C. (or 10° C. or room temperature) and centrifuged at 40 rpm on a "head-over-tail" rotator for 30 hours (or less time if increasing the temperature). Chromatin-antibody-bead complexes are washed four times 100 μL RIPA buffer. The concentration of SDS and NaCl may be titrated for each antibody to find optimal conditions for maximized signal-to-noise ratio. For H3K4me3, RIPA buffer with 0.1% SDS and 140 mM NaCl or 0.2% SDS and 300 mM NaCl, 1×RIPA buffer with 0.23% SDS and 300 mM NaCl followed by 2×RIPA buffer with 0.2% SDS and 300 mM NaCl was used. For H3K27ac, 4×RIPA buffer with 0.1% SDS and 140 mM NaCl was used. Each wash involved rough vortexing on full speed, repeated twice with pauses on ice in between. The next wash used 1×100 μl TE and a tube shift as previously described.

DNA Isolation and Purification. TE is removed and add 150 μl ChIP elution buffer (20 mM Tris-HCl pH 7.5, 50 mM NaCl, 5 mM EDTA. 1% SDS, 30 ug RNase A) is added. Samples are incubated at 37 C, 1 hour at 1200 rpm on a Thermomixer. One ul of Proteinase K (20 mg/ml stock) is added to each tube, followed by incubation at 68° C., 4 hours at 1250 rpm. The eluate is transferred to a 1.5 ml tube and a second elution with 150 μl is performed and pooled with the first supernatant. ChIP DNA is purified by phenol-chloroform isoamylalcohol extraction, ethanol-precipitated with 10 ml acrylamide carrier as described previously and dissolved in 10 μl EB (10 mM Tris-HCl). Alternatively, ChIP DNA is purified with AMPure XP beads or SPRI beads or a similar strategy.

Library preparation and sequencing. ChIP and input library preparation was carried out according to the THRUPlex (Rubicon Genomics) procedure with some modifications including increased incubation times in the library purification and size selection. Twelve ChIP libraries was pooled prior to AMPure XP purification and allowed to bind for 10 minutes after extensive mixing. Increased elution time, thorough mixing the use of a strong neodymium bar magnet allowed for elution in 25 µl EB. Sequencing procedures were carried out as described previously according to Illumina protocols with minor modifications (Illumina, San Diego, Calif.). Alternatively, one can use the QIAGEN library preparation kits, for example QIAseq Ultralow Input Kits.

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A method of performing Chromatin Immunoprecipitation and high throughput sequencing (ChIP-seq), comprising:
    a) sonicating a sample comprising a plurality of cells or embryos under conditions such that chromatin in said cells is fragmented;
    b) contacting said sample with an antibody that specifically binds to a target protein or nucleic acid;
    c) contacting said sample with a combination of IgG antibodies and histone that block non-specific binding of proteins from said sample to said antibody;
    d) washing said sample under stringent conditions;
    e) generating sequencing libraries; and
    f) pooling said sequencing libraries.

2. The method of claim 1, wherein said histone is selected from the group consisting of histone monomers, histone dimers, histone tetramers, and histone octomers.

3. The method of claim 1, wherein said method further comprising the step of performing a sequencing assay with said pooled sequencing library.

4. The method of claim 1, wherein said sample is a single cell or single embryo.

5. The method of claim 4, wherein said sample is a fraction of lysate of a single cell or single embryo.

6. The method of claim 1, wherein said sample is 10 or less cells or embryos.

7. The method of claim 1, wherein said sample of cells is 500 or less cells or embryos.

8. The method of claim 1, wherein said sample of cells is 100,000 or less cells or embryos.

9. The method of claim 1, wherein said embryos are selected from the group consisting of 2 cell embryos, 4 cell embryos, and 8 cell embryos.

10. The method of claim 3, wherein said sequencing assay is a high throughput sequencing assay.

11. The method of claim 2, wherein said histone monomers, dimers, tetramers, or octomers are histone H2A, H2B, H3 and H4 proteins without chemical modifications.

12. The method of claim 1, wherein said antibody that specifically binds to a target protein or nucleic acid is bound to a solid support or free.

13. The method of claim 12, wherein said solid support is magnetic or paramagnetic beads.

14. The method of claim 1, wherein said target protein is a transcription factor, a DNA binding protein, a chromatin binding protein, an RNA binding protein, or a histone.

15. The method of claim 14, wherein said target protein is H3K4me3, H3, or K27ac.

16. The method of claim 2, wherein said histones are cross-linked.

17. The method of claim 2, wherein said histones are native.

18. A method of performing Chromatin Immunoprecipitation and high throughput sequencing (ChIP-seq), comprising:
    a) providing a lysate corresponding to a single cell or single embryo;
    b) contacting said lysate with an epitope binding factor that specifically binds to a target protein or nucleic acid;
    c) contacting said sample with a combination of IgG antibodies and histone that blocks non-specific binding of proteins from said sample to said epitope binding factor antibody;
    d) washing said sample under stringent conditions;
    e) generating sequencing libraries; and
    f) pooling said sequencing libraries.

* * * * *